United States Patent
Rousseau et al.

(10) Patent No.: US 10,690,938 B2
(45) Date of Patent: Jun. 23, 2020

(54) OPHTHALMIC PROGRESSIVE ADDITION LENS FOR A MYOPIC OR EMMETROPIC PRESBYOPIC WEARER; METHOD FOR PROVIDING SUCH A LENS

(71) Applicant: Essilor International, Charenton-le-Pont (FR)

(72) Inventors: Benjamin Rousseau, Charenton-le-Pont (FR); Melanie Heslouis, Charenton-le-Pont (FR); Sebastien Fricker, Charenton-le-Pont (FR); Nacer Lakhchaf, Charenton-le-Pont (FR); Guilhem Escalier, Charenton-le-Pont (FR); Thierry Bonnin, Charenton-le-Pont (FR); Isabelle Poulain, Charenton-le-Pont (FR); Valerie Jolivet, Charenton-le-Pont (FR); Juliette Wierzbicki, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 52 days.

(21) Appl. No.: 15/767,814

(22) PCT Filed: Oct. 11, 2016

(86) PCT No.: PCT/EP2016/074304
§ 371 (c)(1),
(2) Date: Apr. 12, 2018

(87) PCT Pub. No.: WO2017/064041
PCT Pub. Date: Apr. 20, 2017

(65) Prior Publication Data
US 2018/0307059 A1 Oct. 25, 2018

(30) Foreign Application Priority Data

Oct. 15, 2015 (EP) ..................................... 15306644
Oct. 15, 2015 (EP) ..................................... 15306646

(Continued)

(51) Int. Cl.
*G02C 7/02* (2006.01)
*G02C 7/06* (2006.01)
(Continued)

(52) U.S. Cl.
CPC ................ *G02C 7/028* (2013.01); *A61F 2/14* (2013.01); *G02C 7/027* (2013.01); *G02C 7/041* (2013.01); *G02C 7/065* (2013.01); *G02C 7/066* (2013.01)

(58) Field of Classification Search
None
See application file for complete search history.

(56) References Cited

U.S. PATENT DOCUMENTS 6,318,859 B1  11/2001  Baudart et al.
RE42,781 E   10/2011  Bourdoncle et al.
(Continued)

FOREIGN PATENT DOCUMENTS

EP   1 791 014 A1   5/2007
EP   2 211 159 A1   7/2010
(Continued)

OTHER PUBLICATIONS

International Search Report dated Dec. 20, 2016, in PCT/EP2016/074304 filed Oct. 11, 2016.

*Primary Examiner* — Darryl J Collins
*Assistant Examiner* — Journey F Sumlar
(74) *Attorney, Agent, or Firm* — Oblon, McClelland, Maier & Neustadt, L.L.P.

(57) ABSTRACT

An ophthalmic progressive addition lens for a myopic or emmetropic presbyopic wearer which has a prescribed far (Continued)

vision mean refractive power and a non nil prescribed addition, $ADD_p$, the lens having a far vision reference point, a mean refractive power, $PPO(\alpha, \beta)$, a module of resulting astigmatism, $ASR(\alpha, \beta)$, a meridian line, $ML(\alpha, \beta)$, the $(\alpha, \beta)$ functions being determined in as-worn conditions of the lens by the wearer for gaze directions $(\alpha, \beta)$ joining the center of rotation of the eye, CRE, and the lens, wherein $\alpha$ is a lowering angle in degree and $\beta$ is an azimuth angle in degree, and wherein a lens criterion, A1/A2, fulfils: A1/A2≥0.50, wherein: A1=α100%−α85%; A2=α100%−α60%.

15 Claims, 12 Drawing Sheets

(30) Foreign Application Priority Data

Oct. 15, 2015 (EP) ..................................... 15306655
Mar. 21, 2016 (EP) ..................................... 16305312

(51) Int. Cl.
*A61F 2/14* (2006.01)
*G02C 7/04* (2006.01)

(56) References Cited

U.S. PATENT DOCUMENTS

| | | |
|---|---|---|
| 2007/0121063 A1 | 5/2007 | Bourdoncle et al. |
| 2008/0013038 A1 | 1/2008 | Guilloux |
| 2011/0202421 A1 | 8/2011 | Yamakaji |
| 2012/0212705 A1 | 8/2012 | Calixte et al. |
| 2014/0016088 A1 | 1/2014 | De Rossi et al. |
| 2015/0338682 A1 | 11/2015 | Benoit et al. |
| 2016/0306191 A1 | 10/2016 | Marin et al. |

FOREIGN PATENT DOCUMENTS

| | | |
|---|---|---|
| EP | 2 506 063 A1 | 10/2012 |
| EP | 2 752 703 A1 | 7/2014 |
| WO | WO 2006/084986 A1 | 8/2006 |
| WO | WO 2011/042504 A1 | 4/2011 |
| WO | WO 2015/074777 A1 | 5/2015 |

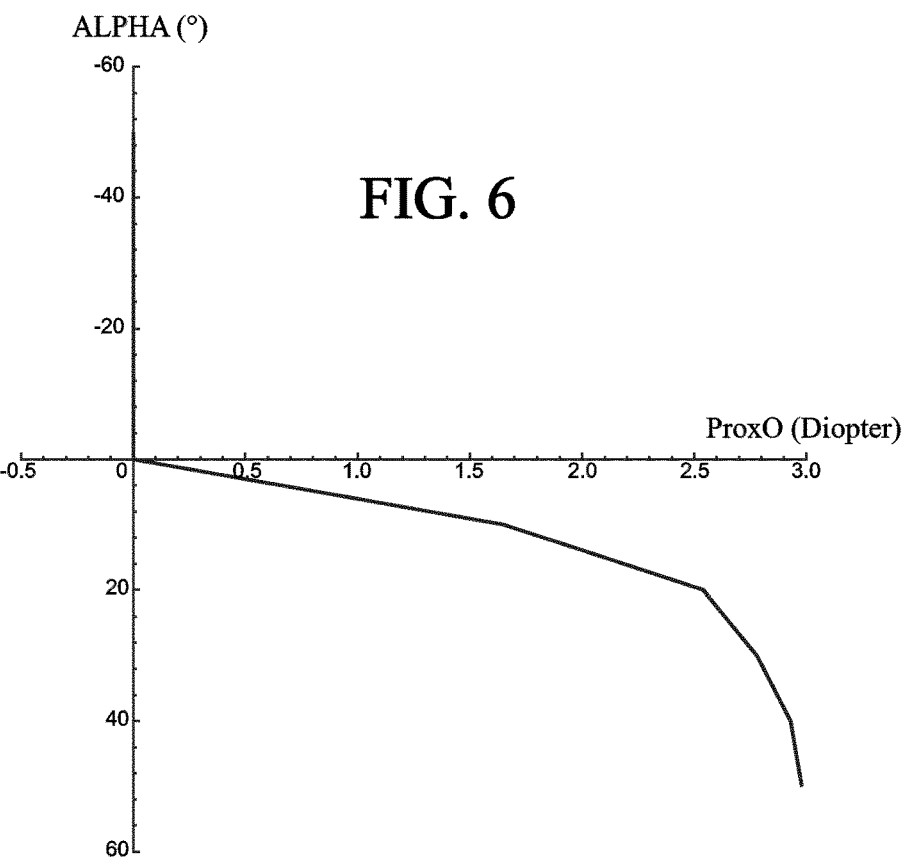
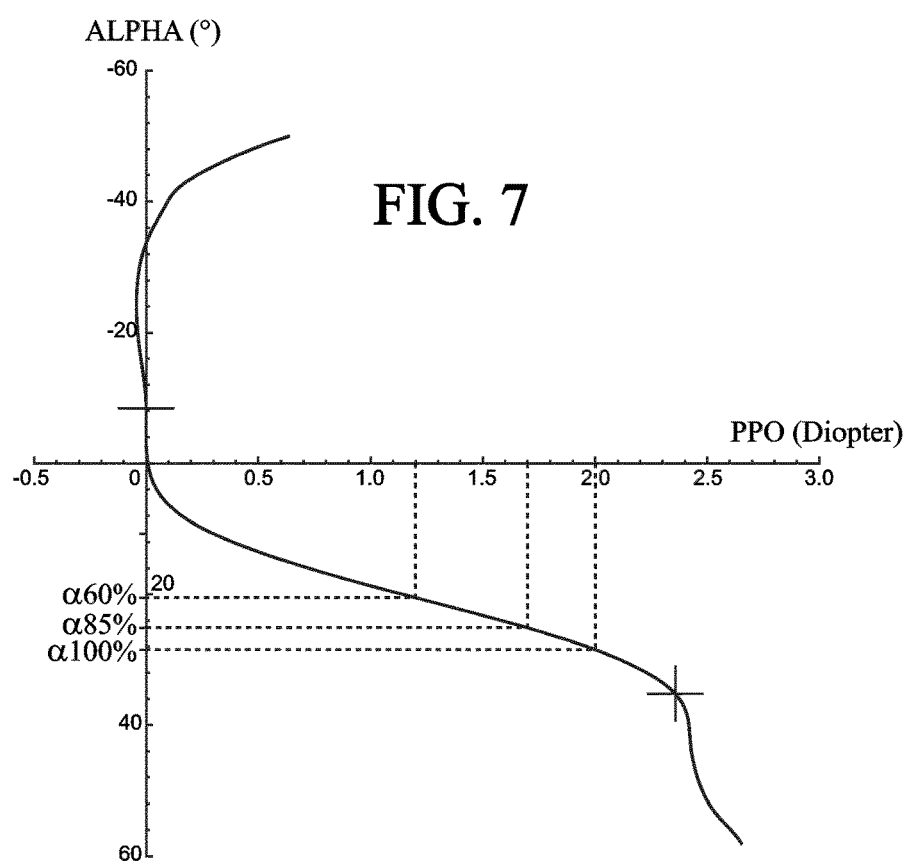

OPHTHALMIC PROGRESSIVE ADDITION LENS FOR A MYOPIC OR EMMETROPIC PRESBYOPIC WEARER; METHOD FOR PROVIDING SUCH A LENS

The invention relates generally to the field of vision improvement and more specifically concerns an ophthalmic progressive addition lens for a myopic and presbyopic wearer, which has a prescribed far vision mean refractive power equal or less to minus 1 Diopter, or for an emmetropic and presbyopic wearer, which has a prescribed far vision mean refractive power greater than minus 1 Diopter and less than plus 1 Diopter. It also relates to a method for providing such a lens.

Conventionally, spectacles lenses are manufactured on request in accordance with specifications intrinsic to individual wearers. Such specifications generally encompass a medical prescription made by an ophthalmologist or an eye care practitioner.

For presbyopic wearers, the value of the power correction is different for far vision and near vision, due to the difficulties of accommodation in near vision. The prescription thus comprises a far-vision power value and an addition representing the power increment between far vision and near vision. The addition is qualified as prescribed addition $ADD_p$.

The inventors have noticed that current ophthalmic progressive addition lens for a myopic or emmetropic presbyopic wearer can still be improved so as to enhance the wearer's visual comfort, especially for visual tasks at distances of 70 cm and less.

A problem that the invention aims to solve is thus to enhance the wearer's visual comfort, especially for visual tasks at distances of 70 cm and less.

For this purpose, a subject of the invention is an ophthalmic progressive addition lens for a myopic and presbyopic wearer, which has a prescribed far vision mean refractive power equal or less to minus 1 Diopter, or for an emmetropic and presbyopic wearer, which has a prescribed far vision mean refractive power greater than minus 1 Diopter and less than plus 1 Diopter, and a non-nil prescribed addition, $ADD_p$, said lens having a far vision reference point, a mean refractive power, $PPO(\alpha, \beta)$, a module of resulting astigmatism, $ASR(\alpha, \beta)$, a meridian line, $ML(\alpha, \beta)$, said $(\alpha, \beta)$ functions being determined in as-worn conditions of the lens by the wearer for gaze directions $(\alpha, \beta)$ joining the center of rotation of the eye, CRE, and the lens, where $\alpha$ is a lowering angle in degree and $\beta$ is an azimuth angle in degree, and wherein a lens criterion, A1/A2, fulfils following requirement:

$A1/A2 \geq 0.50$, where:

A1 = $\alpha100\% - \alpha85\%$;
A2 = $\alpha100\% - \alpha60\%$;
$\alpha100\%$ being the lowering angle corresponding to the minimum positive $\alpha$ angle between:
  the lowering angle where 100% of the prescribed addition is perceived by the wearer on the meridian line,
  the lowering angle where the mean refractive power on the meridian line is maximum, $PPO_{max}(\alpha_{ML}, \beta_{ML})$;
$\alpha85\%$ being the lowering angle where 85% of the prescribed addition is perceived by the wearer on the meridian line;
$\alpha60\%$ being the lowering angle where 60% of the prescribed addition is perceived by the wearer on the meridian line;

$(\alpha_{FV}, \beta_{FV})$ is the far-vision gaze direction, FVGD, defined as the vision gaze direction corresponding to the far vision reference point.

The inventors have discovered that defining a threshold value of a criterion, A1/A2, is suitable to characterize ophthalmic progressive addition lens for a myopic or emmetropic presbyopic wearer where the wearer's visual comfort is enhanced in view of known prior art ophthalmic progressive addition lens, especially for visual tasks at distances of 70 cm and less.

The inventors have further discovered that, thanks to the present invention, fields of vision can be improved in term of acuity for a myopic or emmetropic presbyopic wearer of an ophthalmic progressive addition lens; they have also discovered that peripheral aberration peaks can be reduced. Accordingly, the wearer's visual comfort can be enhanced.

According to different embodiments of the present invention, that may be combined:
$0.50 \leq A1/A2 < 0.54$ or $A1/A2 = 0.54$ or $0.54 < A1/A2 < 0.60$ or $A1/A2 = 0.60$ or $A1/A2 > 0.60$;
The lens fulfils following requirement:

$0.48 \leq CRITER \leq 0.7$, where:

$CRITER = (A1/A2) + (PPO(\alpha_{FV}, \beta_{FV})/(100 \cdot ADD_p))$ $0.48 \leq CRITER < 0.54$ or $CRITER = 0.54$ or
$0.54 < CRITER < 0.58$ or $CRITER = 0.58$ or
$0.58 < CRITER < 0.60$ or $CRITER = 0.60$ or
$0.60 < CRITER \leq 0.70$;
$CRITER \geq 0.50$ and/or $CRITER \leq 0.65$;
The lens is an ophthalmic progressive addition lens for an emmetropic and presbyopic wearer and wherein: $CRITER \geq 0.52$;
The lens is an ophthalmic progressive addition lens for an emmetropic and presbyopic wearer and:
$0.52 \leq CRITER < 0.54$ or $CRITER = 0.54$ or
$0.54 < CRITER < 0.60$ or $CRITER = 0.60$ or
$0.60 < CRITER \leq 0.70$
The lens fulfils following requirement:

$LAcuSub60\_85(0.1) \cdot ADD_p \geq 75$ deg$^2 \cdot D$, wherein:

$LAcuSub60\_85(0.1)$ is the angular extent (in deg$^2$) of the zone of the lens where $ACU(\alpha, \beta) \leq 0.1$ log MAR where $\alpha60\% \geq \alpha \geq \alpha85\%$;
$ACU(\alpha, \beta)$ is the acuity loss value expressed in log MAR and defined according to following equation: $ACU(\alpha, \beta) = -\log(AC\%(\alpha, \beta)/100)$;
$AC\%(\alpha, \beta) = 100 - 63 \times P(\alpha, \beta) - 44.3 \times ASR(\alpha, \beta) + 7.2 \times P(\alpha, \beta)^2 + 19.5 \times P(\alpha, \beta) \times ASR(\alpha, \beta) + ASR(\alpha, \beta)^2$; when $P(\alpha, \beta) \geq 0$; and,
$AC\%(\alpha, \beta) = 100 - 44.3 \times ASR(\alpha, \beta) + ASR(\alpha, \beta)^2$; when $P(\alpha, \beta) < 0$;
$P(\alpha, \beta) = PPO(\alpha, \beta) - PPO(\alpha, \beta\_\alpha\_mer)$;
$\beta\_\alpha\_mer$ is the value of the azimuth angle $\beta$ on the meridian line, $ML(\alpha, \beta)$, at the lowering angle $\alpha$;
The lens fulfils following requirement:

$LAcuSub60\_85(0.2) \cdot ADD_p \geq 135$ deg$^2 \cdot D$, wherein:

$LAcuSub60\_85(0.2)$ is the angular extent (in deg$^2$) of the zone of the lens where $ACU(\alpha, \beta) \leq 0.2$ log MAR where $\alpha60\% \geq \alpha \geq \alpha85\%$;
The lens comprises two main surfaces facing each other wherein said two main surfaces are complex surfaces, as for example two progressive surfaces or two degressive surfaces or a progressive surface and a degressive surface.

In another aspect, the present invention also provides a method implemented by computer means for providing an ophthalmic progressive addition lens to a myopic and presbyopic wearer, which has a prescribed far vision mean refractive power equal or less to minus 1 Diopter, or to an emmetropic and presbyopic wearer, which has a prescribed far vision mean refractive power greater than minus 1 Diopter and less than plus 1 Diopter, and a non nil prescribed addition, $ADD_p$, comprising the step of calculating a mean refractive power repartition, $PPO(\alpha, \beta)$, a module of resulting astigmatism repartition, $ASR(\alpha, \beta)$, calculating a meridian line, $ML(\alpha, \beta)$, where said $(\alpha, \beta)$ functions are calculated in as-worn conditions of the lens by the wearer for gaze directions $(\alpha, \beta)$ joining the center of rotation of the eye, CRE, and the lens, where $\alpha$ is a lowering angle in degree and $\beta$ is an azimuth angle in degree, so as to fulfil following requirement of a criterion, A1/A2:

$A1/A2 \geq 0.50$, where:

A1=$\alpha 100\% - \alpha 85\%$;
A2=$\alpha 100\% - \alpha 60\%$;
$\alpha 100\%$ being the lowering angle corresponding to the minimum positive $\alpha$ angle between:
  the lowering angle where 100% of the prescribed addition is perceived by the wearer on the meridian line,
  the lowering angle where the mean refractive power on the meridian line is maximum, $PPO_{max}(\alpha_{ML}, \beta_{ML})$;
$\alpha 85\%$ being the lowering angle where 85% of the prescribed addition is perceived by the wearer on the meridian line;
$\alpha 60\%$ being the lowering angle where 60% of the prescribed addition is perceived by the wearer on the meridian line;
$(\alpha_{FV}, \beta_{FV})$ is the far-vision gaze direction, FVGD, defined as the vision gaze direction corresponding to the far vision reference point.

According to different embodiments of the method of the present invention, that may be combined, the method further comprising following features:
one calculates the lens so as to fulfil following requirement of a of a criterion, CRITER:

$0.48 \leq CRITER \leq 0.7$, where:

$CRITER = (A1/A2) + (PPO(\alpha_{FV}, \beta_{FV})/(100 \cdot ADD_p))$;

according to an embodiment, $CRITER \geq 0.50$ and/or $CRITER \leq 0.65$;
one calculates the lens so as to fulfil following requirement of a criterion, LAcuSub60_85(0.1):

$LAcuSub60\_85(0.1) \cdot ADD_p \geq 75$ deg$^2 \cdot D$, wherein:

LAcuSub60_85(0.1) is the angular extent (in deg$^2$) of the zone of the lens where $ACU(\alpha, \beta) \leq 0.1$ log MAR where $\alpha 60\% \geq \alpha \geq \alpha 85\%$;
$ACU(\alpha, \beta)$ is the acuity loss value expressed in log MAR and defined according to following equation:
$ACU(\alpha, \beta) = -\log(AC\%(\alpha, \beta)/100)$;
$AC\%(\alpha, \beta) = 100 - 63 \times P(\alpha, \beta) - 44.3 \times ASR(\alpha, \beta) + 7.2 \times P(\alpha, \beta)^2 + 19.5 \times P(\alpha, \beta) \times ASR(\alpha, \beta) + ASR(\alpha, \beta)^2$; when $P(\alpha, \beta) \geq 0$; and,
$AC\%(\alpha, \beta) = 100 - 44.3 \times ASR(\alpha, \beta) + ASR(\alpha, \beta)^2$; when $P(\alpha, \beta) < 0$;
$P(\alpha, \beta) = PPO(\alpha, \beta) - PPO(\alpha, \beta\_\alpha\_mer)$;
$\beta\_\alpha\_mer$ is the value of the azimuth angle $\beta$ on the meridian line, $ML(\alpha, \beta)$, at the lowering angle $\alpha$;

one calculates the lens so as to fulfil following requirement of a criterion, LAcuSub60_85(0.2):

$LAcuSub60\_85(0.2) \cdot ADD_p \geq 135$ deg$^2 \cdot D$, wherein:

LAcuSub60_85(0.2) is the angular extent (in deg$^2$) of the zone of the lens where $ACU(\alpha, \beta) \leq 0.2$ log MAR where $\alpha 60\% \geq \alpha \geq \alpha 85\%$;
the method comprises an optimization routine where at least a target is chosen within the list of requirements related to: criterion A1/A2, criterion CRITER; criterion LAcuSub60_85(0.1); criterion LAcuSub60_85(0.2).

One further underlines that the here above recited features of ophthalmic progressive addition lenses according to the present invention can be directly transposed to the method of the present invention and can be for example introduced as one or as a plurality of target(s) in an optimization routine of said method.

In still another aspect, the present invention relates to a computer program product comprising one or more stored sequence of instruction that is accessible to a processor and which, when executed by the processor, causes the processor to carry out at least one of the steps of the different embodiments of the preceding method.

The invention also relates to a computer-readable medium carrying one or more sequences of instructions of the preceding computer program product.

DESCRIPTION OF THE DRAWINGS

The features of the present invention, as well as the invention itself, both as to its structure and its operation, will be best understood from the accompanying non limiting drawings and examples, taken in conjunction with the accompanying description, in which:

FIGS. 4 to 6 show diagrams helping understanding the definitions of the criteria/data used within the frame of the present invention;

FIGS. 7 to 10 and 15 to 18 give optical characteristics of a plurality of ophthalmic progressive addition lenses according to the prior art;

On the figures, following references correspond to followings:
  MER is the meridian line;
  NVGD is the near vision gaze direction;
  FVGD is the far vision gaze direction;
  FCGD is the fitting cross gaze direction Definitions The following definitions are provided so as to define the wordings used within the frame of the present invention.

The wordings "wearer's prescription", also called "prescription data", are known in the art. Prescription data refers to one or more data obtained for the wearer and indicating for at least an eye, preferably for each eye, a prescribed sphere $SPH_p$, and/or a prescribed astigmatism value $CYL_p$ and a prescribed axis $AXIS_p$ suitable for correcting the ametropia of each eye for the wearer and, if suitable, a prescribed addition $ADD_p$ suitable for correcting the presbyopia of each of his eyes.

"Progressive ophthalmic addition lenses" are known in the art. According to the invention, the lens may be a standard lens but also a lens for information glasses, wherein the lens comprises means for displaying information in front of the eye. The lens may also be suitable for sunglasses or not. All ophthalmic lenses of the invention may be paired so as to form a pair of lenses (left eye LE, right eye RE).

Figure 1:
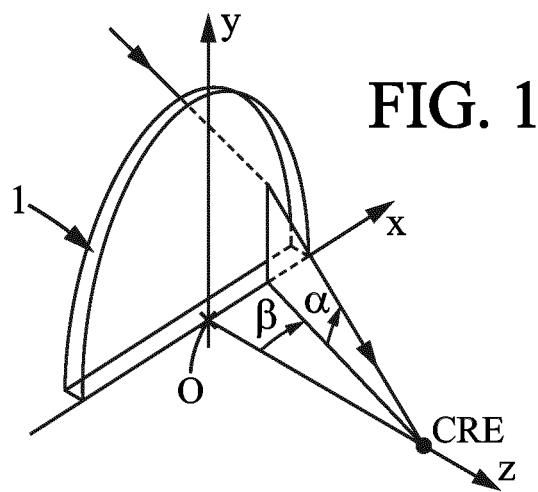
FIGS. 1 and 2 show, diagrammatically, optical systems of eye and lens and ray tracing from the center of rotation of the eye.
Figure 2:
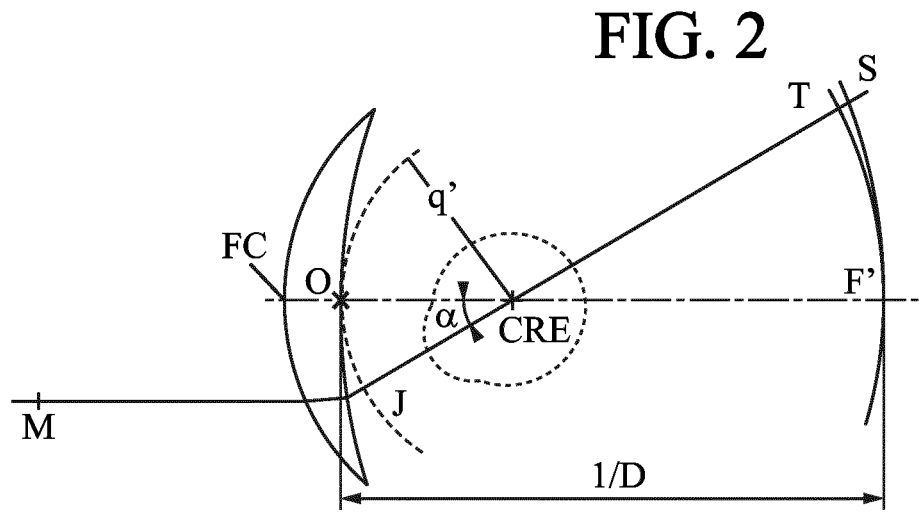

A "gaze direction" is identified by a couple of angle values $(\alpha,\beta)$, wherein said angles values are measured with regard to reference axes centered on the center of rotation of the eye, commonly named as "CRE". More precisely, FIG. 1 represents a perspective view of such a system illustrating parameters $\alpha$ and $\beta$ used to define a gaze direction. FIG. 2 is a view in the vertical plane parallel to the antero-posterior axis of the wearer's head and passing through the center of rotation of the eye in the case when the parameter $\beta$ is equal to 0. The center of rotation of the eye is labeled CRE. The axis CRE-F', shown on FIG. 2 in a dot-dash line, is the horizontal axis passing through the center of rotation of the eye and extending in front of the wearer—that is the axis CRE-F' corresponding to the primary gaze direction. The lens is placed and centered in front of the eye such that the axis CRE-F' cuts the front surface of the lens on a point called the fitting cross, which is, in general, present on lenses to enable the positioning of lenses in a frame by an optician. The point of intersection of the rear surface of the lens and the axis CRE-F' is the point, O. A vertex sphere, which center is the center of rotation of the eye, CRE, and has a radius q'=O-CRE, intercepts the rear surface of the lens in a point of the horizontal axis. A value of radius q' of 25.5 mm corresponds to a usual value and provides satisfying results when wearing the lenses. Other value of radius q' may be chosen. A given gaze direction, represented by a solid line on FIG. 1, corresponds to a position of the eye in rotation around CRE and to a point J (see FIG. 2) of the vertex sphere; the angle $\beta$ is the angle formed between the axis CRE-F' and the projection of the straight line CRE-J on the horizontal plane comprising the axis CRE-F'; this angle appears on the scheme on FIG. 1. The angle $\alpha$ is the angle formed between the axis CRE-J and the projection of the straight line CRE-J on the horizontal plane comprising the axis CRE-F'; this angle appears on the scheme on FIGS. 1 and 2. A given gaze view thus corresponds to a point J of the vertex sphere or to a couple $(\alpha,\beta)$. The more the value of the lowering gaze angle is positive, the more the gaze is lowering and the more the value is negative, the more the gaze is rising. In a given gaze direction, the image of a point M in the object space, located at a given object distance, is formed between two points S and T corresponding to minimum and maximum distances JS and JT, which would be the sagittal and tangential local focal lengths. The image of a point in the object space at infinity is formed, at the point F'. The distance D corresponds to the rear frontal plane of the lens.

For each gaze direction $(\alpha,\beta)$, a mean refractive power $PPO(\alpha,\beta)$, a module of astigmatism $ASR(\alpha,\beta)$ and an axis $AXE(\alpha,\beta)$ of this astigmatism, and a module of resulting (also called residual or unwanted) astigmatism $ASR(\alpha,\beta)$ are defined.

"Astigmatism" refers to astigmatism generated by the lens, or to residual astigmatism (resulting astigmatism) which corresponds to the difference between the prescribed astigmatism (wearer astigmatism) and the lens-generated astigmatism; in each case, with regards to amplitude or both amplitude and axis;

"Ergorama" is a function associating to each gaze direction the usual distance of an object point. Typically, in far vision following the primary gaze direction, the object point is at infinity. In near vision, following a gaze direction essentially corresponding to an angle $\alpha$ of the order of 35° and to an angle $\beta$ of the order of 5° in absolute value towards the nasal side, the object distance is of the order of 30 to 50 cm. For more details concerning a possible definition of an ergorama, U.S. Pat. No. 6,318,859 may be considered. This document describes an ergorama, its definition and its modeling method. For a method of the invention, points may be at infinity or not. Ergorama may be a function of the wearer's ametropia. Using these elements, it is possible to define a wearer optical power and astigmatism, in each gaze direction. An object point M at an object distance given by the ergorama is considered for a gaze direction $(\alpha,\beta)$. An object proximity ProxO is defined for the point M on the corresponding light ray in the object space as the inverse of the distance MJ between point M and point J of the vertex sphere:

$$ProxO = 1/MJ$$

This enables to calculate the object proximity within a thin lens approximation for all points of the vertex sphere, which is used for the determination of the ergorama. For a real lens, the object proximity can be considered as the inverse of the distance between the object point and the front surface of the lens, on the corresponding light ray.

For the same gaze direction $(\alpha,\beta)$, the image of a point M having a given object proximity is formed between two points S and T which correspond respectively to minimal and maximal focal distances (which would be sagittal and tangential focal distances). The quantity ProxI is called image proximity of the point M:

$$ProxI = \frac{1}{2}\left(\frac{1}{JT} + \frac{1}{JS}\right)$$

By analogy with the case of a thin lens, it can therefore be defined, for a given gaze direction and for a given object proximity, i.e. for a point of the object space on the corresponding light ray, an optical power PPO as the sum of the image proximity and the object proximity.

$$PPO = ProxO + ProxI$$

The optical power is also called refractive power.

With the same notations, an astigmatism AST is defined for every gaze direction and for a given object proximity as:

$$AST = \left|\frac{1}{JT} - \frac{1}{JS}\right|$$

This definition corresponds to the astigmatism of a ray beam created by the lens. The resulting astigmatism ASR is defined for every gaze direction through the lens as the difference between the actual astigmatism value AST for this gaze direction and the prescribed astigmatism for the same lens. The residual astigmatism (resulting astigmatism) ASR more precisely corresponds to module of the vectorial difference between actual (AST, AXE) and prescription data $(CYL_p, AXIS_p)$.

When the characterization of the lens is of optical kind, it refers to the ergorama-eye-lens system described above. For simplicity, the term 'lens' is used in the description but it has to be understood as the 'ergorama-eye-lens system'. The values in optic terms can be expressed for gaze directions. Conditions suitable to determine of the ergorama-eye-lens system are called in the frame present invention "as-worn conditions".

In the remainder of the description, terms like «up», «bottom», «horizontal», «vertical», «above», «below», or other words indicating relative position may be used. These terms are to be understood in the wearing conditions of the lens. Notably, the "upper" part of the lens corresponds to a negative lowering angle $\alpha<0°$ and the "lower" part of the lens corresponds to a positive lowering angle $\alpha>0°$.

A "far-vision gaze direction", referred as FVGD, is defined for a lens, as the vision gaze direction corresponding to the far vision (distant) reference point and thus $(\alpha_{FV}, \beta_{FV})$, where the mean refractive power is substantially equal to the mean prescribed power in far vision, the mean prescribed power being equal to $SPH_p+(CYL_p/2)$. Within the present disclosure, far-vision is also referred to as distant-vision.

A "near-vision gaze direction", referred as NVGD, is defined for a lens, as the vision gaze direction corresponding to the near vision (reading) reference point, and thus $(\alpha_{NV}, \beta_{NV})$, where the refractive power is substantially equal to the prescribed power in far vision plus the prescribed addition, $ADD_p$.

A "fitting-cross gaze direction", referred as FCGD, is defined for a lens, as the vision gaze direction corresponding to the fitting cross reference point and thus $(\alpha_{FC}, \beta_{FC})$.

The "meridian line", referred as $ML(\alpha,\beta)$, of a progressive lens is a line defined from top to bottom of the lens and passing through the fitting cross where one can see clearly an object point. Said meridian line is defined on the basis of the repartition of module of resulting astigmatism, ASR, over the $(\alpha, \beta)$ domain and substantially correspond to the center of the two central iso-module of resulting astigmatism values which value is equal to 0.25 Diopter. To be more specific and according to the present invention the meridian line is calculated according to following method:

One defines the gaze direction, FCGD, corresponding to the fitting cross $(\alpha_{FC}, \beta_{FC})$;

One calculates the lowering angle $\alpha_{NV}$ corresponding to the near vision gaze direction;

For each lowering angle $\alpha$ comprised between $\alpha_{FC}$ and $\alpha_{NV}$, one calculates the azimuth angle $\beta$ corresponding to the midway direction between the two central iso-module of resulting astigmatism values which value is equal to 0.25 Diopter; said calculated directions are referred as $(\alpha_i, \beta_i)$; one calculates a straight line, d2, so as to minimizes the deviation of $(\alpha_i, \beta_i)$ to said straight line, according to following equation:

$$d2:\ \beta(\alpha) = a_2\alpha + b_2;\ \alpha_{FC} < \alpha < \alpha_{NV}$$

$$a_2, b_2:\ \min\left\{\sum_i (a_2\alpha_i + b_2 - \beta_i)^2\right\}$$

where «min» function relates to determining the $a_2$ and $b_2$ parameters so as to minimize the equation between brackets.

One calculates a pivot direction $(\alpha_{piv}, \beta_{piv})$ defined as the intersection between the straight line d2 and a line corresponding to $\beta=\beta_{FC}$, where $$:\begin{cases} \alpha_{PIV} = \dfrac{(\beta_{FC} - b_2)}{a_2} \\ \beta_{PIV} = \beta_{FC} \end{cases}$$

One calculates a straight line, d1, where: d1: $\beta(\alpha)=\beta_{PIV}$; $\alpha<\alpha_{PIV}$;

One determines $\beta_{NV}$ as being the azimuth angle $\beta$ of straight line d2 for $\alpha_{NV}$; where: $\beta_{NV}=a_2\alpha_{NV}+b_2$;

For each lowering angle $\alpha$ greater than $\alpha_{NV}$, one determines the azimuth angle $\beta$ corresponding to the midway direction between the two central iso-module of resulting astigmatism values which value is equal to 0.25 Diopter; said calculated directions are referred as $(\alpha_j, \beta_j)$; one calculates a straight line, d3, so as to minimizes the deviation of $(\alpha_j, \beta_j)$ to said straight line and that passes at the direction $(\alpha_{NV}, \beta_{NV})$; if the calculated slope is negative, the sloped is chosen to be nil; d3 is thus defined according to following equation:

$$d3:\ \beta(\alpha) = a_3(\alpha - \alpha_{NV}) + \beta_{NV};\ \alpha_{NV} < \alpha$$

$$a_3:\ \min\left\{\sum_j (a_3(\alpha_j - \alpha_{NV}) + \beta_{NV} - \beta_j)^2;\ a_3 \geq 0\right\}$$

The meridian line is finally defined as being the line built when following the three segments d1, d2, d3.

"Complex surface" is an aspherical surface of an ophthalmic lens which is non-spherical, non-toroidal, non-sphero toroidal; according to an embodiment, a complex surface is chosen within the list consisting of a progressive surface and a degressive surface.

"Micro-markings" also called "alignment reference marking" have been made mandatory on progressive lenses by the harmonized standards ISO 13666:2012 ("Alignment reference marking: permanent markings provided by the manufacturer to establish the horizontal alignment of the lens or lens blank, or to re-establish other reference points") and ISO 8990-2 ("Permanent marking: the lens has to provide at least following permanent markings: alignment reference markings comprising two markings distant from 34 mm one of each other, equidistant from a vertical plane passing through the fitting cross or the prism reference point"). Micro-markings that are defined the same way are also usually made on complex surfaces, such as on a front surface of a lens with a front surface comprising a progressive or regressive front surface.

"Temporary markings" may also be applied on at least one of the two surfaces of the lens, indicating positions of control points (reference points) on the lens, such as a control point for far-vision, a control point for near-vision, a prism reference point and a fitting cross for instance. The prism reference point PRP is considered here at the midpoint of the straight segment which connects the micro-markings. If the temporary markings are absent or have been erased, it is always possible for a skilled person to position the control points on the lens by using a mounting chart and the permanent micro-markings. Similarly, on a semi-finished lens blank, standard ISO 10322-2 requires micro-markings to be applied. The centre of the aspherical surface of a semi-finished lens blank can therefore be determined as well as a referential as described above.

Figure 3:
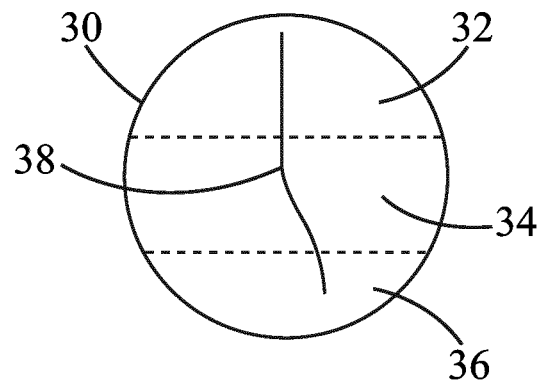
FIG. 3 shows field vision zones of an ophthalmic progressive addition lens.

FIG. 3 shows field vision zones of an ophthalmic progressive addition lens 30 where said lens comprises a far vision (distant vision) zone 32 located in the upper part of the lens, a near vision zone 36 located in the lower part of the lens and an intermediate zone 34 situated between the far vision zone 32 and the near vision zone 36. The meridian line is referred as 38.

Figure 4:
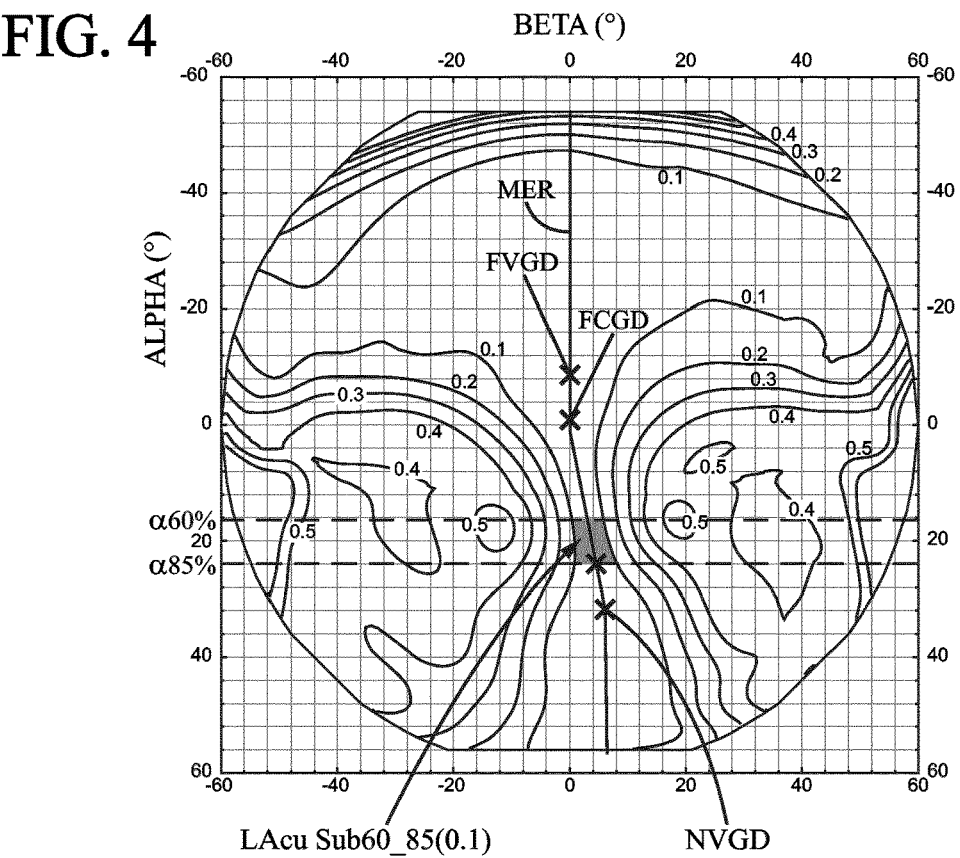
Figure 5:
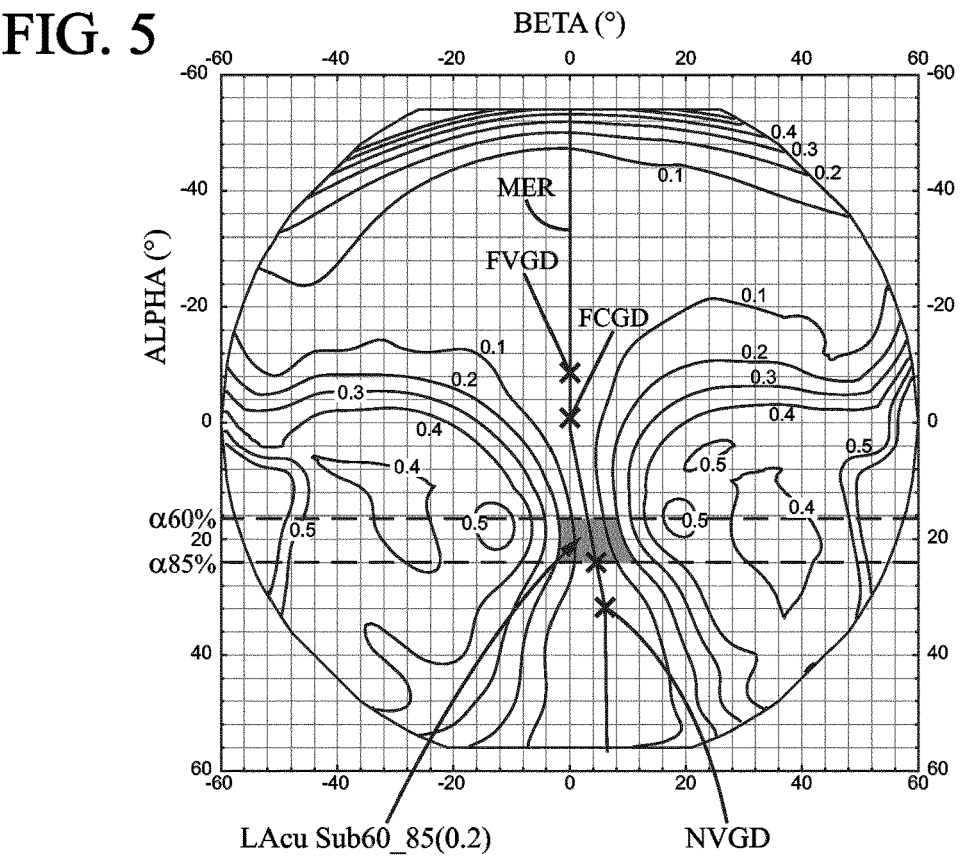

A plurality of criteria/data has been defined in the scope of the present invention and there definitions are illustrated by FIGS. 4 and 5.

In the background of FIGS. 4 and 5, the acuity loss contour plot of a same example of an ophthalmic progressive addition lens is represented.

The acuity loss contour shows the variations over the ($\alpha$, $\beta$) domain of the acuity loss value ACU($\alpha$, $\beta$); the acuity loss value is expressed in log MAR. The acuity loss value ACU($\alpha$, $\beta$) is defined according to following equation:

$$ACU(\alpha,\beta) = -\log(AC\%(\alpha,\beta)/100);$$

AC %($\alpha$, $\beta$) is an acuity function defined as a function of both mean refractive power, PPO($\alpha$, $\beta$), and module of resulting astigmatism, ASR($\alpha$, $\beta$); where:
one defines a mean refractive power difference function, P($\alpha$, $\beta$), where:

$$P(\alpha, \beta) = PPO(\alpha, \beta) - PPO(\alpha,\beta\_\alpha\_mer);$$

$\beta\_\alpha\_mer$ being the value of the azimuth angle $\beta$ on the meridian line, ML($\alpha$, $\beta$), at the lowering angle $\alpha$;
if P($\alpha$, $\beta$)≥0, AC %($\alpha$, $\beta$) is defined according to following equation:

$$AC\%(\alpha,\beta) = \{100 - 63 \times P(\alpha,\beta) - 44.3 \times ASR(\alpha,\beta) + 7.2 \times P(\alpha,\beta)^2 + 19.5 \times P(\alpha,\beta) \times ASR(\alpha,\beta) + ASR(\alpha,\beta)^2\}$$

if P($\alpha$, $\beta$)<0, AC %($\alpha$, $\beta$) is defined according to following equation:

$$AC\%(\alpha,\beta) = 100 - 44.3 \times ASR(\alpha,\beta) + ASR(\alpha,\beta)^2.$$

Bibliographical reference of such an acuity loss definition can be found in following document: Fauquier, C., et al. "Influence of combined power error and astigmatism on visual acuity." *Vision Science and Its Applications, OSA Technical Digest Series. Washington, D.C.: Optical Society of America* (1995): 151-4.

Acuity loss values ACU($\alpha$, $\beta$) of the example lens are plotted in the background of FIGS. 4 and 5 and curves indicates iso-acuity loss values where there is an increment of 0.1 log MAR between neighbouring curves of different acuity loss values.

FIG. 4 shows how to calculate criterion LAcuSub60_85 (0.1); LAcuSub60_85(0.1) is the angular extent (in deg$^2$) of the zone (in grey on the figure) between the two central neighbouring curves of acuity loss equal to 0.1 log MAR, said angular extent being calculated for lowering angle $\alpha$ equal or greater to $\alpha$60% (i.e. for $\alpha$≥$\alpha$60%) and for lowering angle $\alpha$ equal or less than $\alpha$85% (i.e. for $\alpha$≤$\alpha$85%).

$\alpha$85% is defined as the lowering angle where 85% of the prescribed addition is perceived by the wearer on the meridian line. The lowering angle of the meridian line where 85% of the prescribed addition is perceived by the wearer is defined in the frame of the present invention as being the angle lowering a where the mean refractive power, PPO ($\alpha$85%), fulfills following equation:

$$PPO(\alpha 85\%) = PPO(FVGD) + 0.85 \times ADD_p,$$

and where PPO(FVGD) is the mean refractive power according to the far-vision gaze direction, FVGD.

Similar definition is used for $\alpha$60% which is a lowering angle of the meridian line where 60% of the prescribed addition is perceived by the wearer which corresponds to the lowering angle $\alpha$ where the mean refractive power, PPO ($\alpha$60%), fulfills following equation:

$$PPO(\alpha 60\%) = PPO(FVGD) + 0.60 \times ADD_p.$$

$\alpha$100% is defined as the lowering angle corresponding to the minimum positive $\alpha$ angle between:
the lowering angle where 100% of the prescribed addition is perceived by the wearer on the meridian line,
the lowering angle where the mean refractive power on the meridian line is maximum, $PPO_{max}(\alpha_{ML}, \beta_{ML})$;
In the examples that are further recited, $\alpha$100% is a lowering angle of the meridian line where 100% of the prescribed addition is perceived by the wearer which corresponds to the lowering angle $\alpha$ where the mean refractive power, PPO($\alpha$100%), fulfills following equation:

$$PPO(\alpha 100\%) = PPO(FVGD) + ADD_p.$$

If no lowering angle of the meridian line fulfils the previous equation, $\alpha$100% is the lowering angle where the mean refractive power on the meridian line is maximum, $PPO_{max}(\alpha_{ML}, \beta_{ML})$.

FIG. 5 shows how to calculate criterion LAcuSub60_85 (0.2); LAcuSub60_85(0.2) is the angular extent (in deg$^2$) of the zone (in grey on the figure) between the two central neighbouring curves of acuity loss equal to 0.2 log MAR, said angular extent being calculated for lowering angle $\alpha$ equal or greater to $\alpha$60% (i.e. for $\alpha$≥$\alpha$60%) and for lowering angle $\alpha$ equal or less than $\alpha$85% (i.e. for $\alpha$≤$\alpha$85%).

FIG. 6 shows the variation of object proximity ProxO as a function of the lowering angle $\alpha$ used to define the ergorama in view of U.S. Pat. No. 6,318,859.

The ergorama used in the frame of the present invention is defined thanks to following data, where object proximity values are given for lowering angles $\alpha$:

| Alpha [deg] | ProxO [D] |
|---|---|
| −50 | 0 |
| −40 | 0 |
| −30 | 0 |
| −20 | 0 |
| −10 | 0 |
| 0 | 0 |
| 10 | 1.65 |
| 20 | 2.54 |
| 30 | 2.78 |
| 40 | 2.93 |
| 50 | 2.98 |

Examples

Ophthalmic Progressive Addition Lenses for a Myopic and Presbyopic Wearer which has a Prescribed Far Vision Mean Refractive Power Equal or Less to Minus 1 Diopter:

FIGS. 7 to 10 give optical characteristics of an ophthalmic progressive addition lens for a myopic and presbyopic wearer according to the prior art, hereafter referred as "PA_lens_myopic".

FIGS. 11 to 14 give optical characteristics of an ophthalmic progressive addition lens for a myopic and presbyopic wearer according to the invention, hereafter referred as "INV_lens_myopic".

Figure 11:
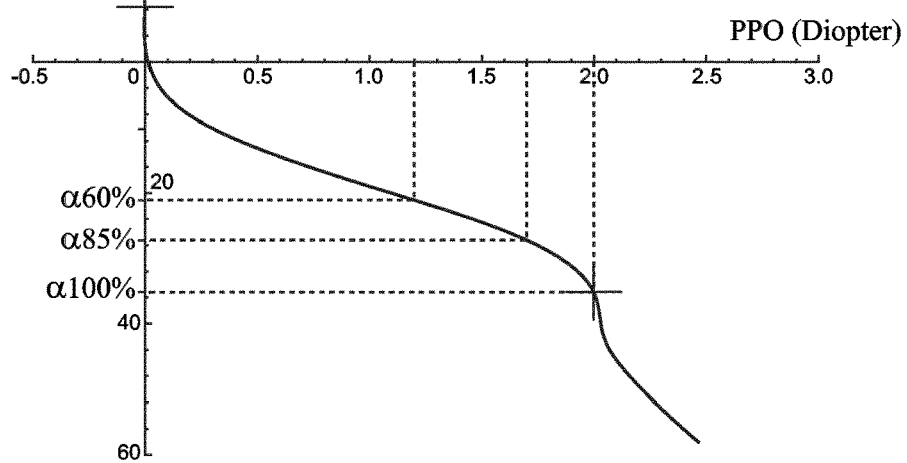
FIGS. 11 to 14 and 19 to 25 give optical characteristics of a plurality of ophthalmic progressive addition lenses according to the invention.

Said both ophthalmic progressive addition lenses have been designed so as to fulfil following prescribed features:

prescribed sphere $SPH_p=-4$ Diopter
prescribed astigmatism value $CYL_p=0$ Diopter
prescribed axis $AXIS_p=0°$
prescribed addition $ADD_p=2$ Diopter FIGS. 7 and 11 represent the mean refractive power repartition profile, PPO, as a function of the lowering angle α, along the meridian line, for respectively the prior art ophthalmic progressive addition lens and the ophthalmic progressive addition lens according to the present invention. Lowering angles corresponding to α60%, α85% and to α100% are indicated.

Figure 8:
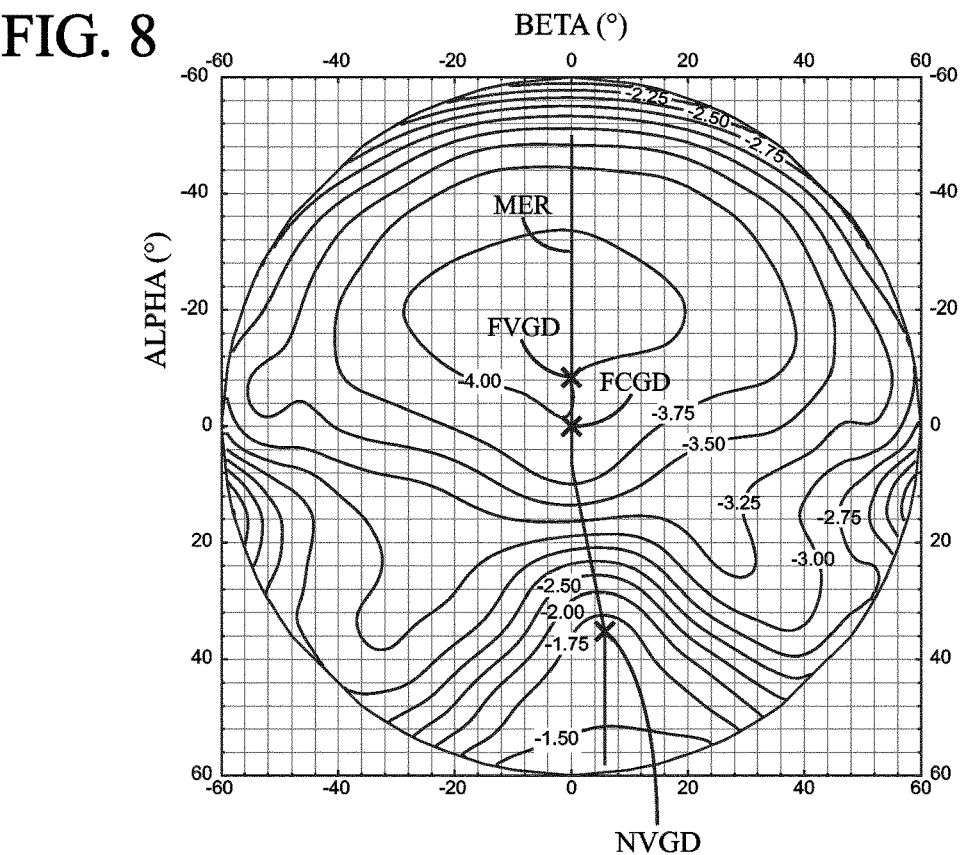
Figure 12:
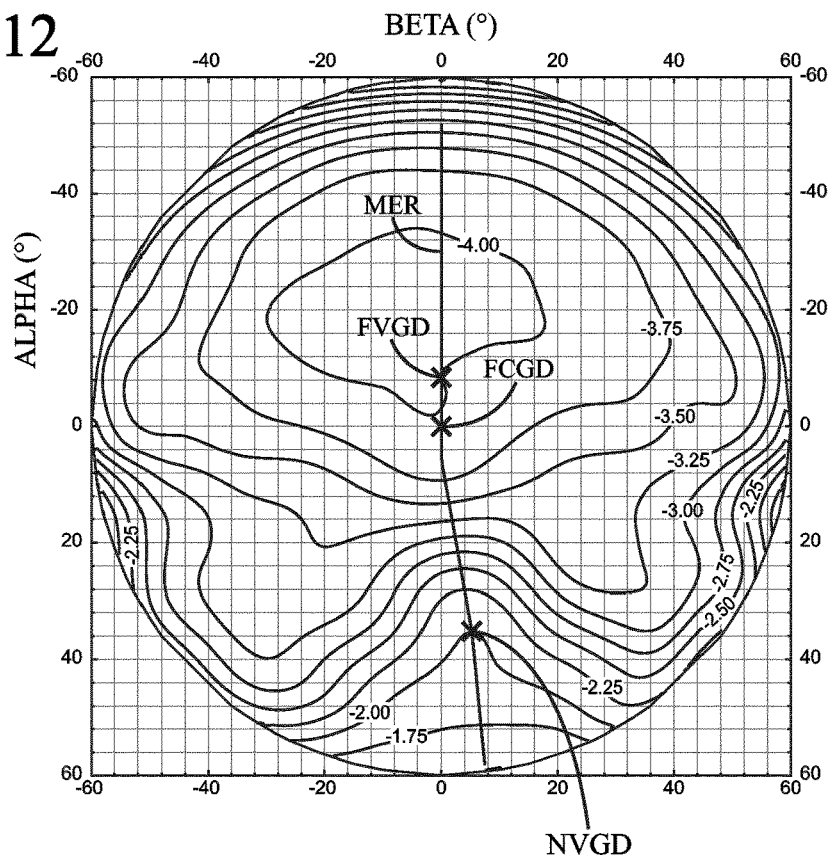

FIGS. 8 and 12 represent the mean refractive power repartition, PPO, over the (α, β) domain, for respectively the prior art ophthalmic progressive addition lens and the ophthalmic progressive addition lens according to the present invention. Curves indicates iso-mean refractive power values where there is an increment of 0.25 Diopter between neighbouring curves of different module of resulting astigmatism values.

Figure 9:
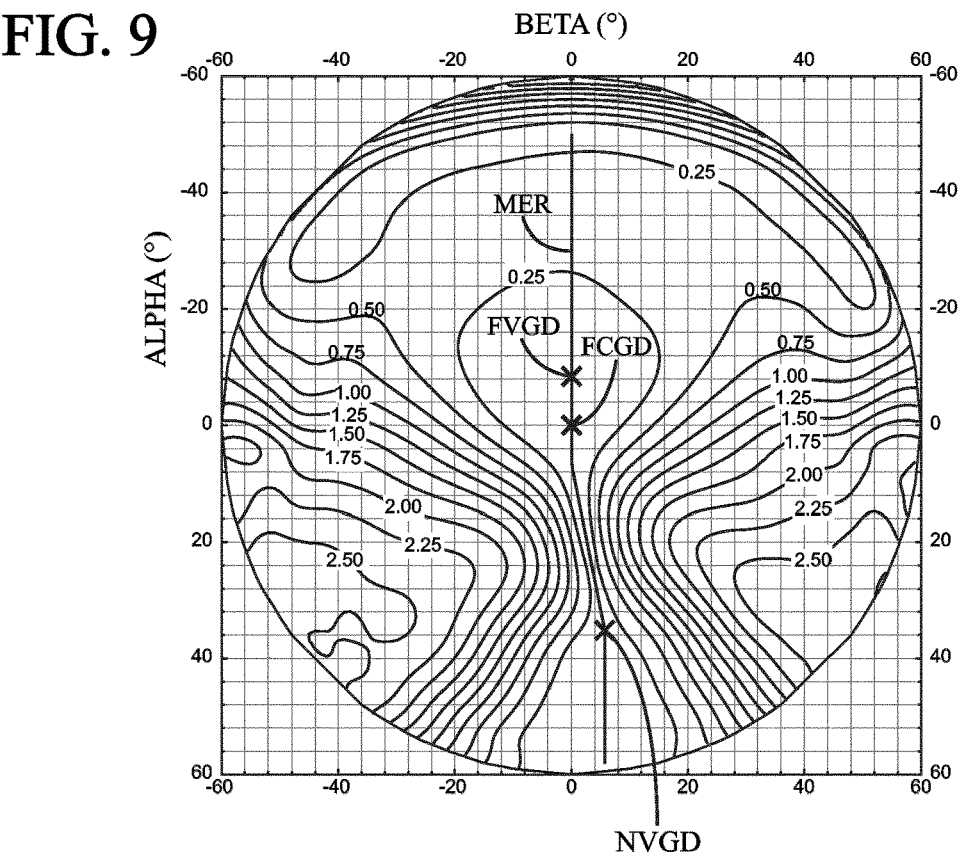
Figure 13:
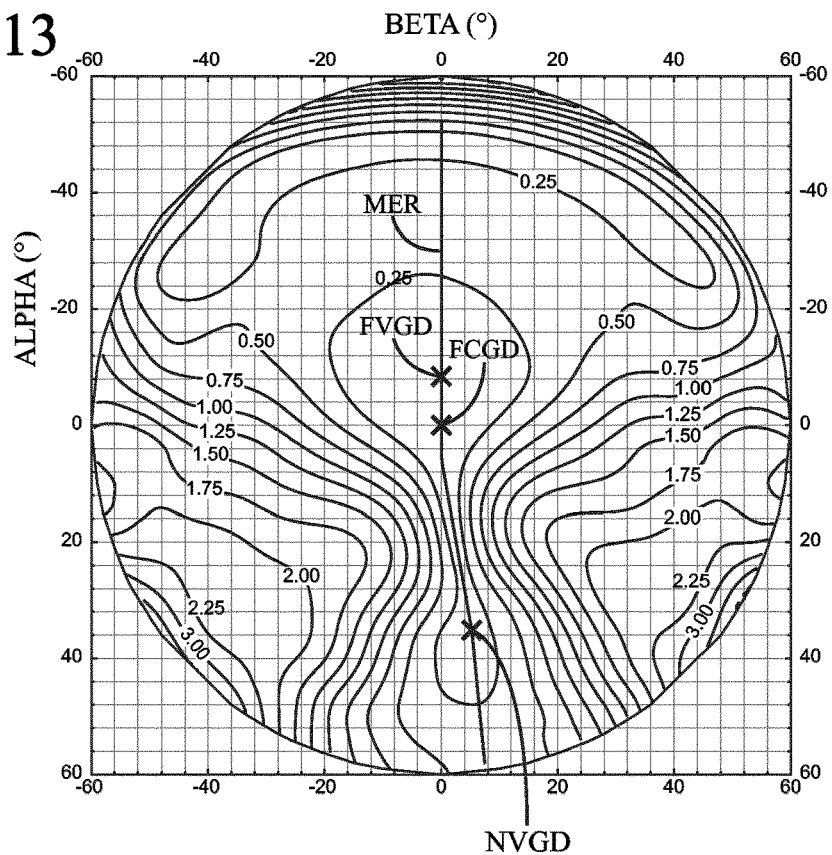

FIGS. 9 and 13 represent the module of resulting astigmatism repartition, ASR, over the (α, β) domain, for respectively the prior art ophthalmic progressive addition lens and the ophthalmic progressive addition lens according to the present invention. Curves indicates iso-module of resulting astigmatism values where there is an increment of 0.25 Diopter between neighbouring curves of different module of resulting astigmatism values.

Figure 10:
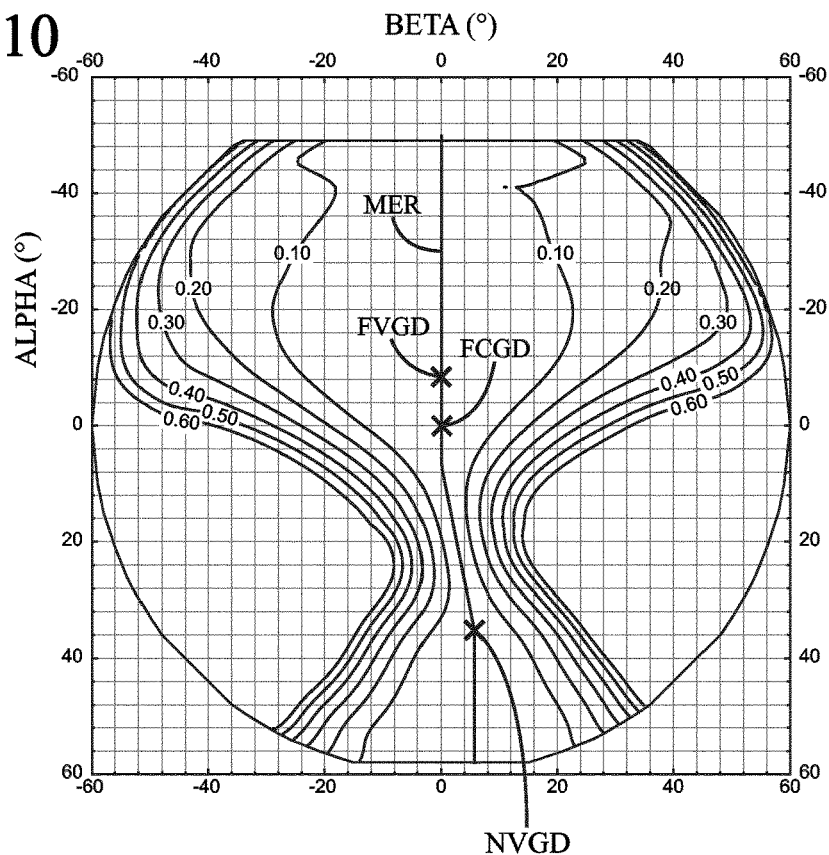
Figure 14:
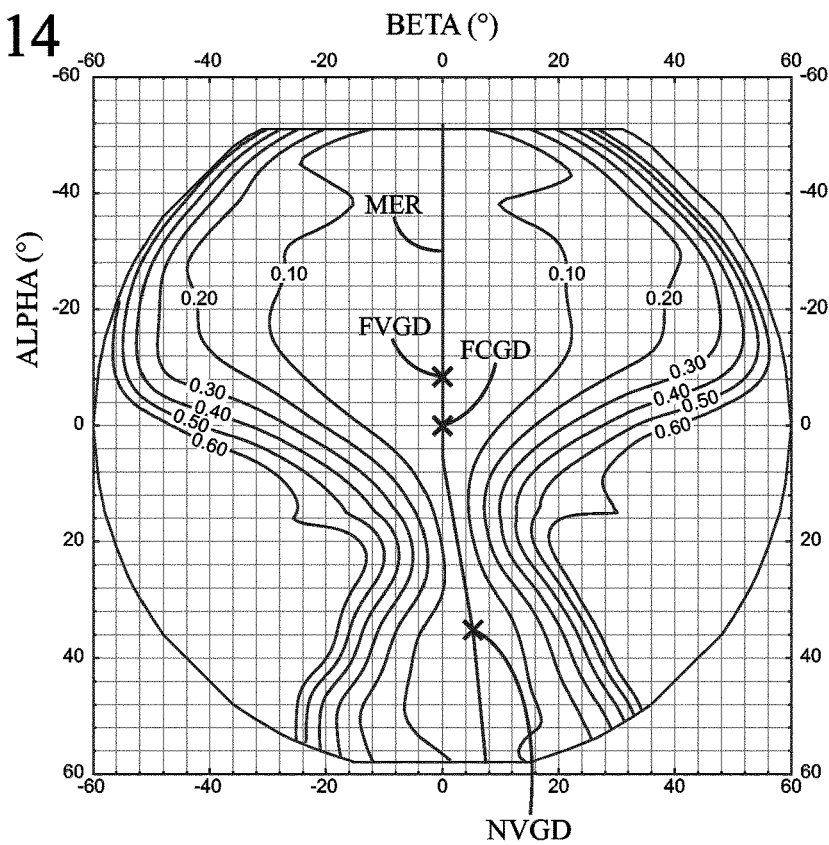

FIGS. 10 and 14 represent the acuity loss value repartition ACU, over the (α, β) domain, for respectively the prior art ophthalmic progressive addition lens and the ophthalmic progressive addition lens according to the present invention. Curves indicates iso-acuity loss values where there is an increment of 0.1 log MAR between neighbouring curves of different module of resulting astigmatism values.

Here above defined criteria have been calculated for the said both ophthalmic progressive addition lenses. Results are reported here bellow:

| Lens | PA_lens_myopic | INV_lens_myopic |
|---|---|---|
| A1/A2 | 0.40 | 0.60 |
| CRITER | 0.38 | 0.58 |
| LAcuSub60_85(0.1).$ADD_p$ | 62 | 94 |
| LAcuSub60_85(0.2).$ADD_p$ | 108 | 160 | presbyopic wearer according to the invention, hereafter referred as "INV_lens_em1".

Figure 23:
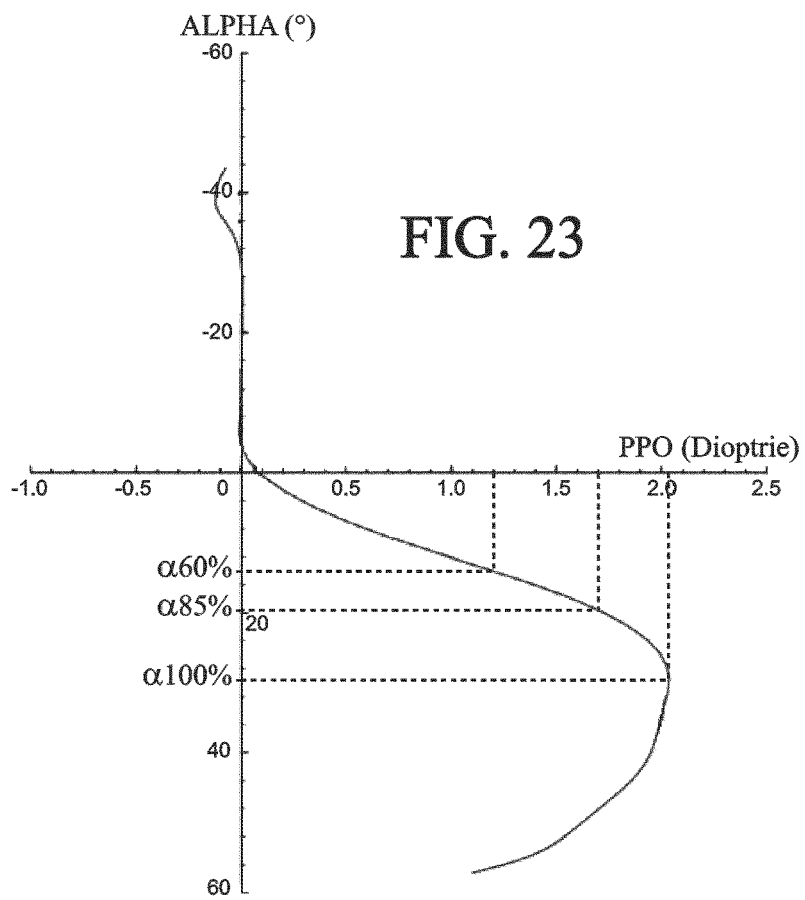
Figure 24:
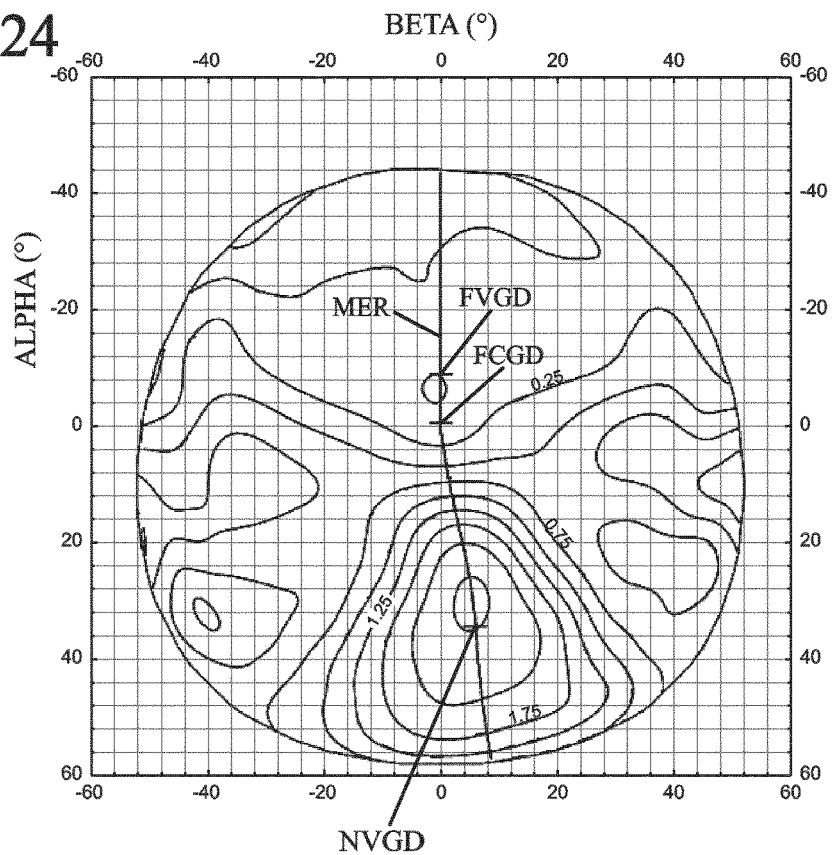
Figure 25:
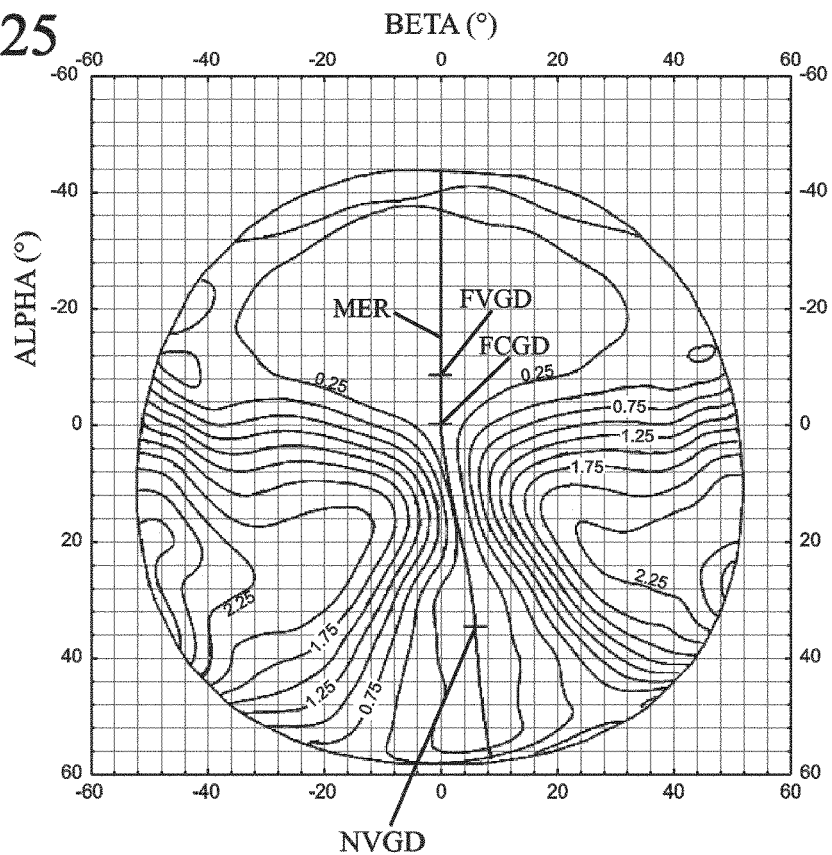

FIGS. 23 to 25 give optical characteristics of a second ophthalmic progressive addition lens for an emmetropic and presbyopic wearer according to the invention, hereafter referred as "INV_lens_em2".

Figure 15:
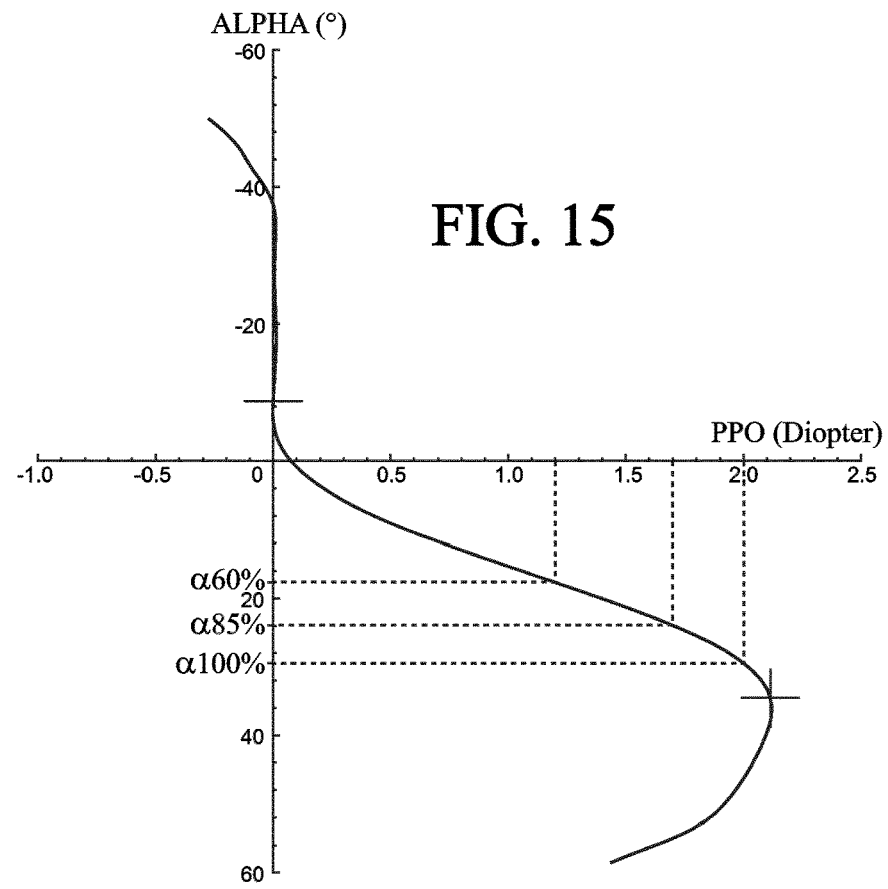
Figure 19:
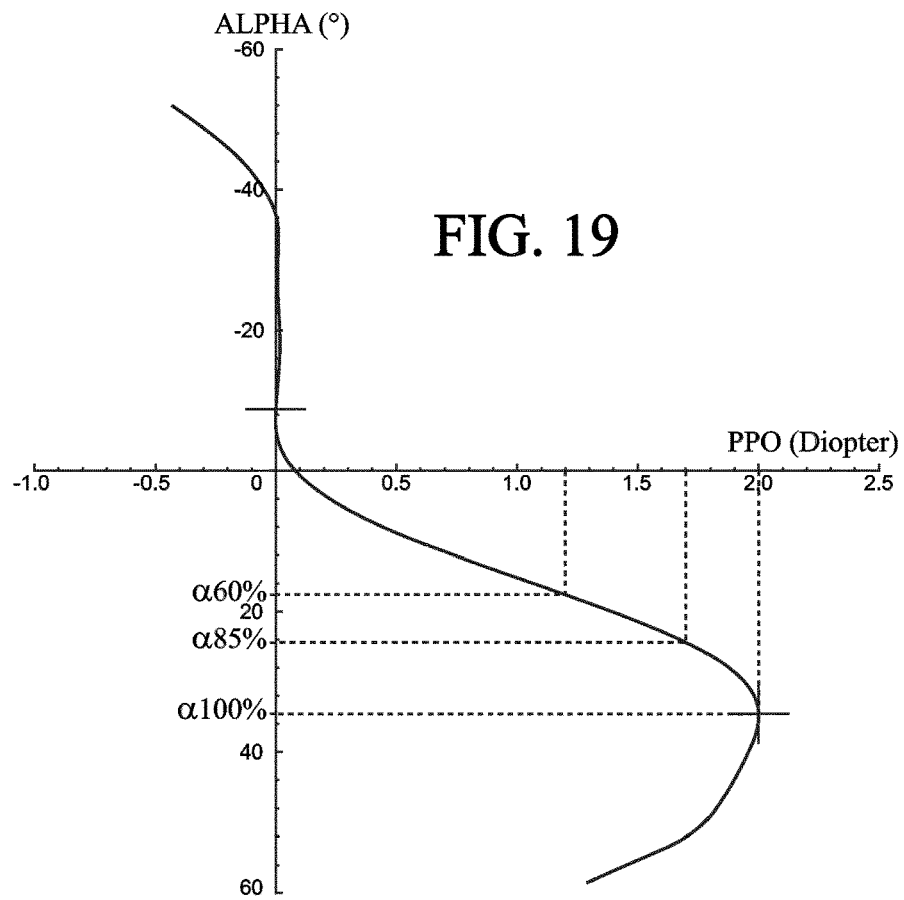

Said three ophthalmic progressive addition lenses have been designed so as to fulfil following prescribed features:
prescribed sphere $SPH_p=0$ Diopter
prescribed astigmatism value $CYL_p=0$ Diopter
prescribed axis $AXIS_p=0°$
prescribed addition $ADD_p=2$ Diopter FIGS. 15, 19 and 23 represent the mean refractive power repartition profile, PPO, as a function of the lowering angle α, along the meridian line, for respectively the prior art ophthalmic progressive addition lens and the ophthalmic progressive addition lenses according to the present invention referred as INV_lens_em1 and INV_lens_em2. Here above comments directed to FIGS. 7 and 11 are transferred to the present figures.

Figure 16:
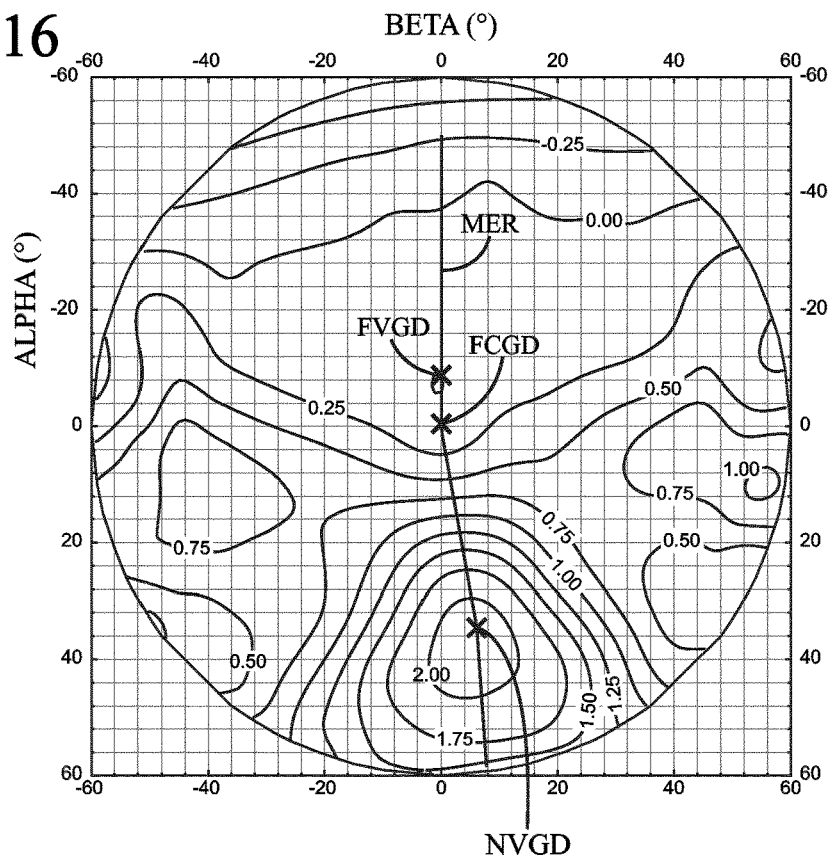
Figure 20:
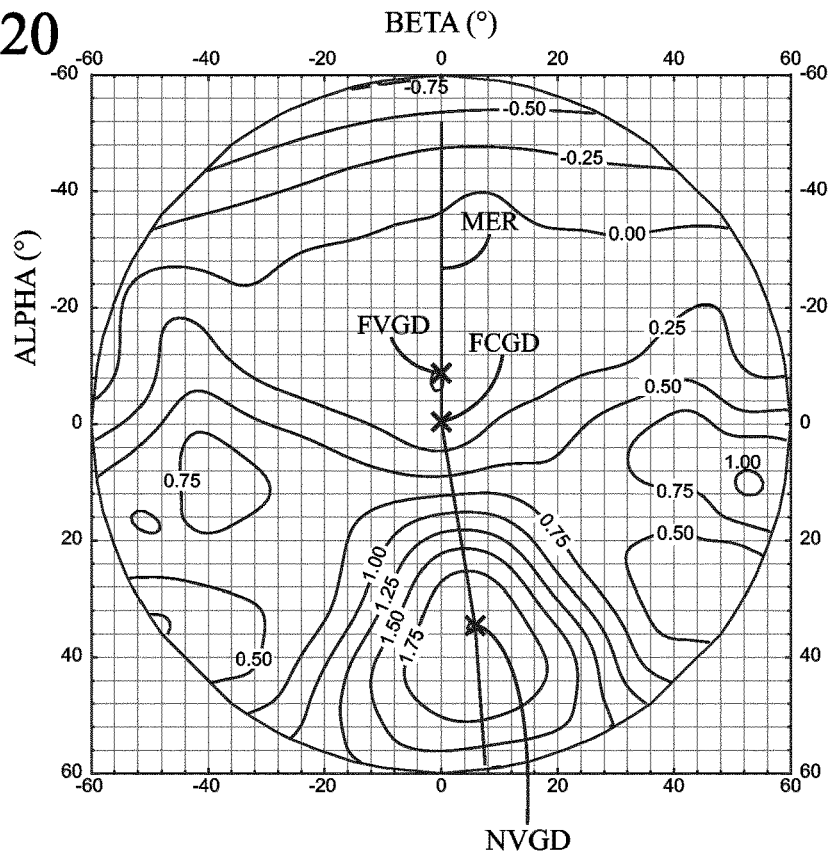

FIGS. 16, 20 and 24 represent the mean refractive power repartition, PPO, over the (α, β) domain, for respectively the prior art ophthalmic progressive addition lens and the ophthalmic progressive addition lenses according to the present invention referred as INV_lens_em1 and INV_lens_em2. Here above comments directed to FIGS. 8 and 12 are transferred to the present figures.

Figure 17:
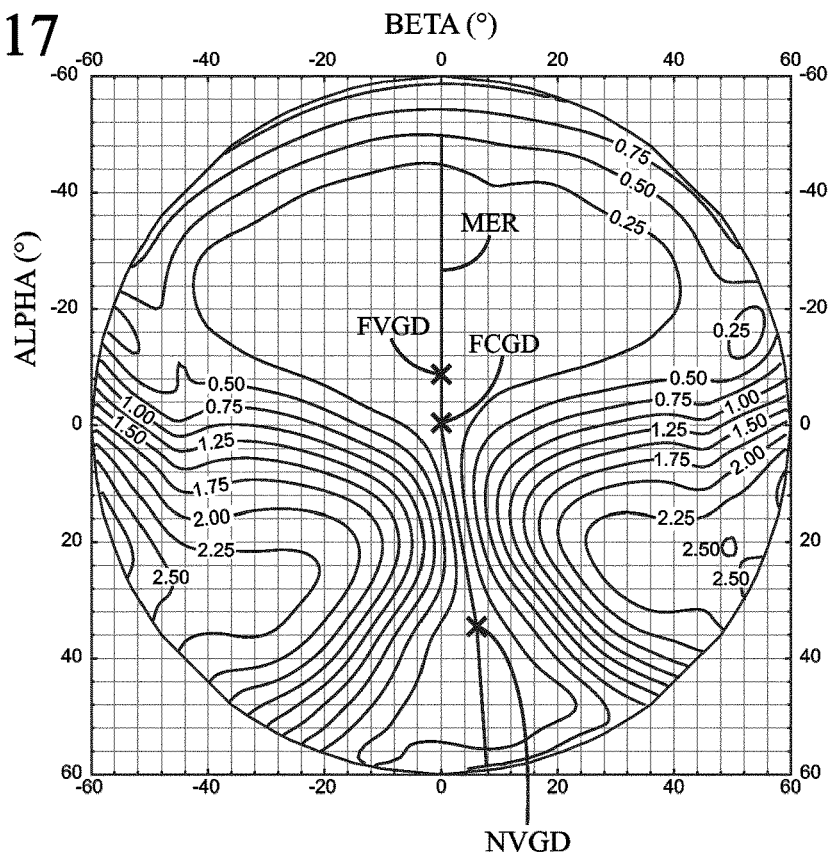
Figure 21:
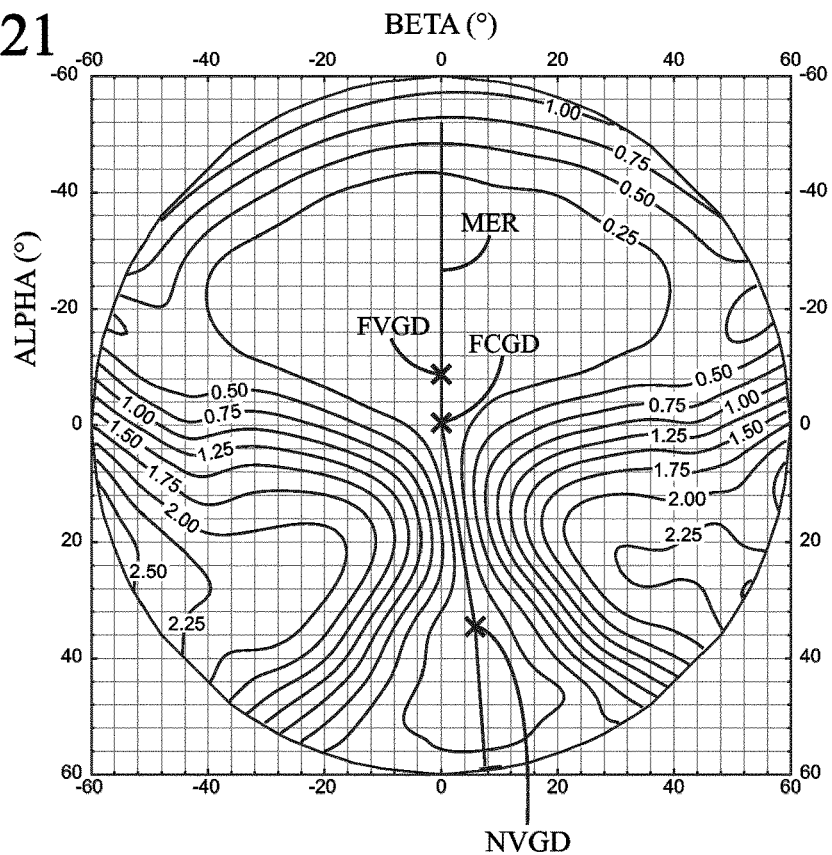

FIGS. 17, 21 and 25 represent the module of resulting astigmatism repartition, ASR, over the (α, β) domain, for respectively the prior art ophthalmic progressive addition lens and the ophthalmic progressive addition lenses according to the present invention referred as INV_lens_em1 and INV_lens_em2. Here above comments directed to FIGS. 9 and 13 are transferred to the present figures.

Figure 18:
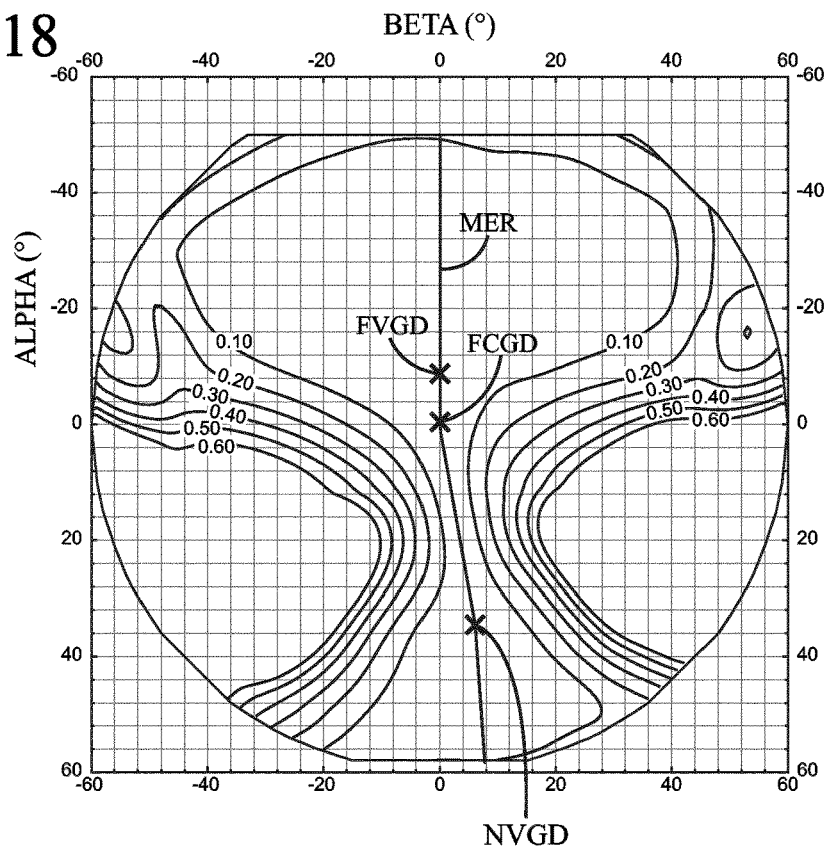
Figure 22:
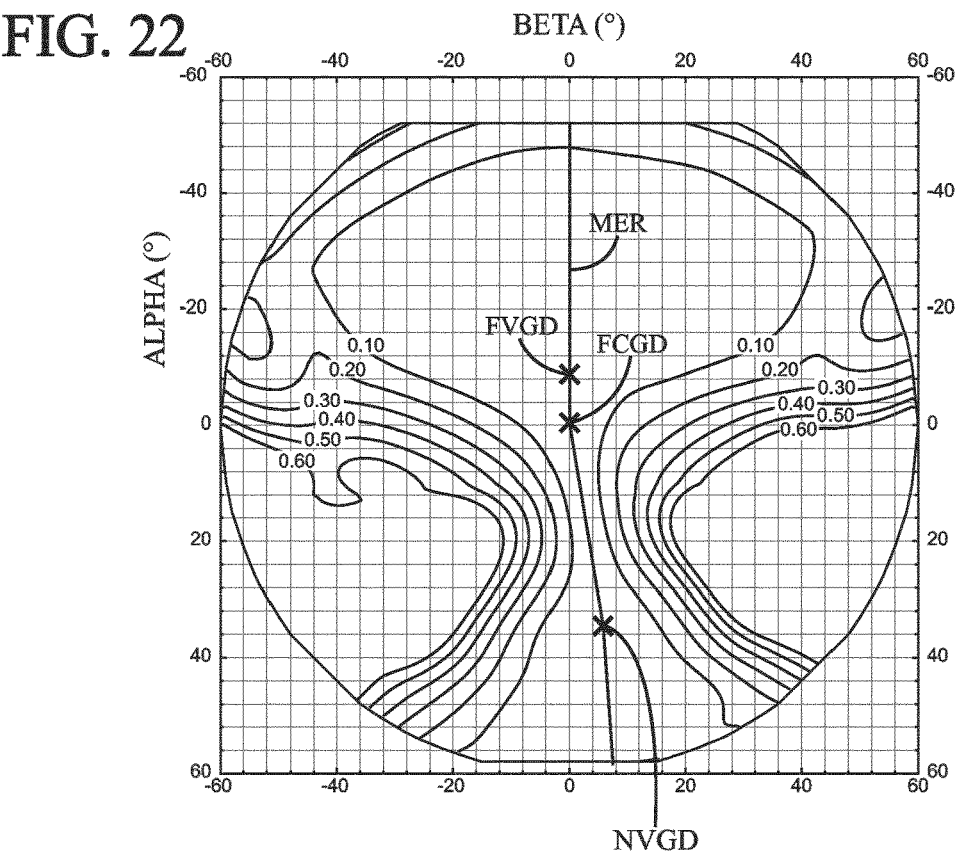

FIGS. 18 and 22 represent the acuity loss value repartition ACU, over the (α, β) domain, for respectively the prior art ophthalmic progressive addition lens and the ophthalmic progressive addition lens according to the present invention referred as INV_lens_em1. Here above comments directed to FIGS. 10 and 14 are transferred to the present figures.

Here above defined criteria have been calculated for the said both ophthalmic progressive addition lenses. Results are reported here below:

| Lens | PA_lens_em | INV_lens_em1 | INV_lens_em2 |
|---|---|---|---|
| A1/A2 | 0.45 | 0.54 | 0.60 |
| CRITER | 0.45 | 0.54 | 0.60 |
| LAcuSub60_85(0.1).$ADD_p$ | 90 | 112 | 80 |
| LAcuSub60_85(0.2).$ADD_p$ | 150 | 196 | 144 |

LAcuSub60_85(0.1)·$ADD_p$ and LAcuSub60_85(0.2)·$ADD_p$ are expressed in $deg^2·D$.

Ophthalmic Progressive Addition Lenses for an Emmetropic and Presbyopic Wearer which has a Prescribed Far Vision Mean Refractive Power Greater than Minus 1 Diopter and Less than Plus 1 Diopter:

FIGS. 15 to 18 give optical characteristics of an ophthalmic progressive addition lens for an emmetropic and presbyopic wearer according to the prior art, hereafter referred as "PA_lens_em".

FIGS. 19 to 22 give optical characteristics of a first ophthalmic progressive addition lens for an emmetropic and The inventors have done tests that demonstrate that the chosen threshold value of CRITER, and optionally the chosen threshold values of LAcuSub60_85(0.1)·$ADD_p$ and/or LAcuSub60_85(0.2)·$ADD_p$, is (are) suitable for providing to a myopic or emmetropic presbyopic wearer an ophthalmic progressive addition lens where the wearer's visual comfort is enhanced in view of known prior art ophthalmic progressive addition lens.

More specifically, the inventors have demonstrated that fulfilling the requirements of CRITER according to the present invention is beneficial for handling the variation of mean refractive power along the meridian line of a progressive addition lens, namely for visual tasks within a 70 cm sphere, for a myopic or emmetropic presbyopic wearer. It has also been demonstrated that the wearer's comfort is accordingly significantly enhanced, namely for said visual tasks, and that vision satisfaction for visual tasks within a 70 cm sphere play a very significant role in the global wearer's visual comfort and satisfaction.

The invention claimed is:

1. An ophthalmic progressive addition lens for a myopic and presbyopic wearer, which has a prescribed far vision mean refractive power equal or less to minus 1 Diopter, or for an emmetropic and presbyopic wearer, which has a prescribed far vision mean refractive power greater than minus 1 Diopter and less than plus 1 Diopter, and a non nil prescribed addition, $ADD_p$, said lens having a far vision reference point, a mean refractive power, $PPO(\alpha, \beta)$, a module of resulting astigmatism, $ASR(\alpha, \beta)$, a meridian line, $ML(\alpha, \beta)$, said $(\alpha, \beta)$ functions being determined in as-worn conditions of the lens by the wearer for gaze directions $(\alpha, \beta)$ joining the center of rotation of the eye, CRE, and the lens, where $\alpha$ is a lowering angle in degree and $\beta$ is an azimuth angle in degree, and wherein a lens criterion, A1/A2, fulfils following requirement:

$A1/A2 \geq 0.54$, where:

$A1 = \alpha100\% - \alpha85\%$;
$A2 = \alpha100\% - \alpha60\%$;
$\alpha100\%$ being the lowering angle corresponding to the minimum positive $\alpha$ angle between:
the lowering angle where 100% of the prescribed addition is perceived by the wearer on the meridian line,
the lowering angle where the mean refractive power on the meridian line is maximum, $PPO_{max}(\alpha_{ML}, \beta_{ML})$;
$\alpha85\%$ being the lowering angle where 85% of the prescribed addition is perceived by the wearer on the meridian line;
$\alpha60\%$ being the lowering angle where 60% of the prescribed addition is perceived by the wearer on the meridian line;
$(\alpha_{FV}, \beta_{FV})$ is the far-vision gaze direction, FVGD, defined as the vision gaze direction corresponding to the far vision reference point.

2. An ophthalmic progressive addition lens as claimed in claim 1, according to which a lens criterion, CRITER, fulfils following requirement $0.48 \leq CRITER \leq 0.7$, where:

$CRITER = (A1/A2) + (PPO(\alpha_{FV}, \beta_{FV})/(100 \cdot ADD_p))$.

3. An ophthalmic progressive addition lens as claimed in claim 1, according to which $CRITER \geq 0.50$ and/or $CRITER \leq 0.65$.

4. An ophthalmic progressive addition lens as claimed in claim 3, according to which said lens is an ophthalmic progressive addition lens for an emmetropic and presbyopic wearer and wherein:

$CRITER \geq 0.52$.

5. An ophthalmic progressive addition lens as claimed in claim 1, according to which said lens is an ophthalmic progressive addition lens for an emmetropic and presbyopic wearer and wherein:

$CRITER \geq 0.52$.

6. An ophthalmic progressive addition lens as claimed in claim 1, according to which said lens fulfils following requirement: $LAcuSub60\_85(0.1) \cdot ADD_p \geq 75$ $deg^2 \cdot D$, wherein:

$LAcuSub60\_85(0.1)$ is the angular extent (in $deg^2$) of the zone of the lens where $ACU(\alpha, \beta) \leq 0.1$ log MAR where $\alpha60\% \geq \alpha \geq \alpha85\%$;
$ACU(\alpha, \beta)$ is the acuity loss value expressed in log MAR and defined according to following equation: $ACU(\alpha, \beta) = -\log(AC\%(\alpha, \beta)/100)$;
$AC\%(\alpha, \beta) = 100 - 63 \times P(\alpha, \beta) - 44.3 \times ASR(\alpha, \beta) + 7.2 \times P(\alpha, \beta)^2 + 19.5 \times P(\alpha, \beta) \times ASR(\alpha, \beta) + ASR(\alpha, \beta)^2$; when $P(\alpha, \beta) \geq 0$; and,
$AC\%(\alpha, \beta) = 100 - 44.3 \times ASR(\alpha, \beta) + ASR(\alpha, \beta)^2$; when $P(\alpha, \beta) < 0$;
$P(\alpha, \beta) = PPO(\alpha, \beta) - PPO(\alpha, \beta\_\alpha\_mer)$;
$\beta\_\alpha\_mer$ is the value of the azimuth angle $\beta$ on the meridian line, $ML(\alpha, \beta)$, at the lowering angle $\alpha$.

7. An ophthalmic progressive addition lens as claimed in claim 1, according to which said lens fulfils following requirement: $LAcuSub60\_85(0.2) \cdot ADD_p \geq 135$ $deg^2 \cdot D$, wherein:

$LAcuSub60\_85(0.2)$ is the angular extent (in $deg^2$) of the zone of the lens where $ACU(\alpha, \beta) \leq 0.2$ log MAR where $\alpha60\% \geq \alpha \geq \alpha85\%$.

8. An ophthalmic progressive addition lens as claimed in claim 1, according to which said lens comprises two main surfaces facing each other wherein said two main surfaces are complex surfaces, as for example two progressive surfaces or two degressive surfaces or a progressive surface and a degressive surface.

9. An ophthalmic progressive addition lens as claimed in claim 8, according to which said two main surfaces which are complex surfaces are two progressive surfaces or two degressive surfaces or a progressive surface and a degressive surface.

10. A method implemented by computer means for providing an ophthalmic progressive addition lens to a myopic and presbyopic wearer, which has a prescribed far vision mean refractive power equal or less to minus 1 Diopter, or to an emmetropic and presbyopic wearer, which has a prescribed far vision mean refractive power greater than minus 1 Diopter and less than plus 1 Diopter, and a non nil prescribed addition, $ADD_p$, comprising the step of calculating a mean refractive power repartition, $PPO(\alpha, \beta)$, a module of resulting astigmatism repartition, $ASR(\alpha, \beta)$, calculating a meridian line, $ML(\alpha, \beta)$, where said $(\alpha, \beta)$ functions are calculated in worn conditions of the lens by the wearer for gaze directions $(\alpha, \beta)$ joining the center of rotation of the eye, CRE, and the lens, where $\alpha$ is a lowering angle in degree and $\beta$ is an azimuth angle in degree, so as to fulfil following requirement of a criterion, A1/A2:

$A1/A2 \geq 0.54$, where:

$A1 = \alpha100\% - \alpha85\%$;
$A2 = \alpha100\% - \alpha60\%$;
$\alpha100\%$ being the lowering angle corresponding to the minimum positive $\alpha$ angle between:
the lowering angle where 100% of the prescribed addition is perceived by the wearer on the meridian line,
the lowering angle where the mean refractive power on the meridian line is maximum, $PPO_{max}(\alpha_{ML}, \beta_{ML})$;
$\alpha85\%$ being the lowering angle where 85% of the prescribed addition is perceived by the wearer on the meridian line;
$\alpha60\%$ being the lowering angle where 60% of the prescribed addition is perceived by the wearer on the meridian line;
$(\alpha_{FV}, \beta_{FV})$ is the far-vision gaze direction, FVGD, defined as the vision gaze direction corresponding to the far vision reference point.

11. The method for providing an ophthalmic progressive addition lens as claimed in claim 10, according to which one calculates the lens so as to fulfil following requirement of a criterion, CRITER:

$$0.48 \leq CRITER \leq 0.7, \text{ where:}$$

$$CRITER = (A1/A2) + (PPO(\alpha_{FV}, \beta_{FV})/(100 \cdot ADD_p)).$$

12. The method for providing an ophthalmic progressive addition lens as claimed in claim 11, according to which one calculates the lens so as to fulfil the requirement of the criterion CRITER wherein CRITER≥0.50 and/or CRITER≤0.65.

13. The method for providing an ophthalmic progressive addition lens as claimed in claim 10, according to which one calculates the lens so as to fulfil following requirement of a criterion, LAcuSub60_85(0.1):

$$LAcuSub60\_85(0.1) \cdot ADD_p \geq 75 \text{ deg}^2 \cdot D, \text{ wherein:}$$

LAcuSub60_85(0.1) is the angular extent (in deg$^2$) of the zone of the lens where ACU($\alpha$, $\beta$)≤0.1 log MAR where $\alpha 60\% \geq \alpha \geq \alpha 85\%$;

ACU($\alpha$, $\beta$) is the acuity loss value expressed in log MAR and defined according to following equation: ACU($\alpha$, $\beta$)=−log (AC %($\alpha$, $\beta$)/100);

AC %($\alpha$, $\beta$)=100−63×P($\alpha$, $\beta$)−44.3×ASR($\alpha$, $\beta$)+7.2×P($\alpha$, $\beta$)$^2$+19.5×P($\alpha$, $\beta$)×ASR($\alpha$, $\beta$)+ASR($\alpha$, $\beta$)$^2$; when P($\alpha$, $\beta$)≥0; and, AC %($\alpha$, $\beta$)=100−44.3×ASR($\alpha$, $\beta$)+ASR($\alpha$, $\beta$)$^2$; when P($\alpha$, $\beta$)<0;

P($\alpha$, $\beta$)=PPO($\alpha$, $\beta$)−PPO($\alpha$, $\beta\_\alpha\_$mer);

$\beta\_\alpha\_$mer is the value of the azimuth angle $\beta$ on the meridian line, ML($\alpha$, $\beta$), at the lowering angle $\alpha$.

14. The method for providing an ophthalmic progressive addition lens as claimed in claim 10, according to which one calculates the lens so as to fulfil following requirement of a criterion, LAcuSub60_85(0.2):

$$LAcuSub60\_85(0.2) \cdot ADD_p \geq 135 \text{ deg}^2 \cdot D, \text{ wherein:}$$

LAcuSub60_85(0.2) is the angular extent (in deg$^2$) of the zone of the lens where ACU($\alpha$, $\beta$)≤0.2 log MAR where $\alpha 60\% \geq \alpha \geq \alpha 85\%$.

15. The method for providing an ophthalmic progressive addition lens as claimed in claim 10, according to which the method comprises an optimization routine where at least a target is chosen within the list of requirements related to: criterion A1/A2, criterion CRITER; criterion LAcuSub60_85(0.1); criterion LAcuSub60_85(0.2).

* * * * *